United States Patent
Yu

(10) Patent No.: US 9,155,912 B2
(45) Date of Patent: Oct. 13, 2015

(54) METHOD AND SYSTEM FOR STEREOTACTIC INTENSITY-MODULATED ARC THERAPY

(71) Applicant: Xinsheng Cedric Yu, Pasadena, MD (US)

(72) Inventor: Xinsheng Cedric Yu, Pasadena, MD (US)

(*) Notice: Subject to any disclaimer, the term of this patent is extended or adjusted under 35 U.S.C. 154(b) by 0 days.

(21) Appl. No.: 14/147,553

(22) Filed: Jan. 5, 2014

(65) Prior Publication Data
US 2015/0190658 A1 Jul. 9, 2015

(51) Int. Cl.
*A61B 6/00* (2006.01)
*A61N 5/10* (2006.01)

(52) U.S. Cl.
CPC ............... *A61N 5/1082* (2013.01); *A61N 5/10* (2013.01); *A61N 5/1048* (2013.01)

(58) Field of Classification Search
CPC .......... A61B 5/0555; A61B 6/00; A61B 6/02; A61B 6/022; A61N 2005/1087; A61N 5/10; A61N 5/1048; A61N 5/1084
USPC ................... 600/1–8, 439; 378/20; 250/492.3
See application file for complete search history.

(56) References Cited

U.S. PATENT DOCUMENTS

| | | | |
|---|---|---|---|
| 6,259,762 B1 | 7/2001 | Pastyr et al. | |
| 7,473,913 B2 * | 1/2009 | Hermann et al. | 250/492.3 |
| 2002/0003854 A1 * | 1/2002 | Ivan et al. | 378/20 |
| 2010/0036245 A1 * | 2/2010 | Yu et al. | 600/439 |
| 2011/0210261 A1 | 9/2011 | Maurer | |
| 2011/0301449 A1 | 12/2011 | Maurer | |
| 2012/0189102 A1 | 7/2012 | Maurer et al. | |

OTHER PUBLICATIONS

Adler et al., "CyberKnife image-guided radiosurgery for brain and spinal tumors," *International Congress Series*, 1247: 545-552 (2002).
Bhatnagar et al., "First year experience with newly developed Leksell Gamma Knife Perfexion," *J. Med. Phys.*, 34(3): 141-148 (2009).

(Continued)

*Primary Examiner* — Christine H Matthews
(74) *Attorney, Agent, or Firm* — Carol Larcher; Larcher & Chao Law Group

(57) ABSTRACT

A method of irradiating a target in a patient comprising directing a beam of radiation from an external source of radiation 24 at the target in the patient from numerous directions in a broad solid angle by longitudinally rotating the external source of radiation 24 around a central axis and simultaneously or sequentially, in either order, latitudinally rotating the external source of radiation 24; a globe gantry 21 comprising (i) a front opening ring 22 with its origin on the central axis of the globe gantry 21, (ii) at least one arc-shaped, gantry support arm 23, which has a front end and a rear end and is part of a circle, (iii) an external source of radiation 24, which is mounted on at least one arc-shaped, gantry support arm 23, (iv) a rear rotational axle 25 with an axis along the central axis of the globe gantry 21, (v) a support base 27, and (vi) a rear housing 26 comprising a source of power, mechanisms for moving components of the globe gantry 21, and controllers for controlling the movement of the components of the globe gantry 21 and the irradiation of the target in the patient; a system 20 comprising the globe gantry 21; and a method of irradiating a target in a patient using the system.

13 Claims, 13 Drawing Sheets

(56) References Cited

OTHER PUBLICATIONS

Detorie, "Helical Tomotherapy: A new tool for radiation therapy," *J. Amer. Coll. Radiol.*, 5(1): 63-66 (2008).

Erratum in: Veldeman et al., "Evidence behind use of intensity-modulated radiotherapy: A systematic review of comparative clinical studies," *Lancet Oncology*, 9(4): 513 (2008).

Timmerman et al., "Stereotactic Body Radiation Therapy," *Curr. Probl. Canc.*, 29(3): 120-157 (2005).

Veldeman et al., "Evidence behind use of intensity-modulated radiotherapy: A systematic review of comparative clinical studies," *Lancet Oncology*, 9(4): 367-375 (2008).

Yu, et al., "GammaPod—A new device dedicated for stereotactic radiotherapy of breast cancer," *Med. Phys.*, 40(5): 051703-1-051703-11 (2013).

Yu, "Intensity modulated arc therapy using dynamic multi-leaf collimation: An alternative to Tomotherapy," *Phys. Med. Biol.*, 40(9): 1435-1449 (1995).

* cited by examiner

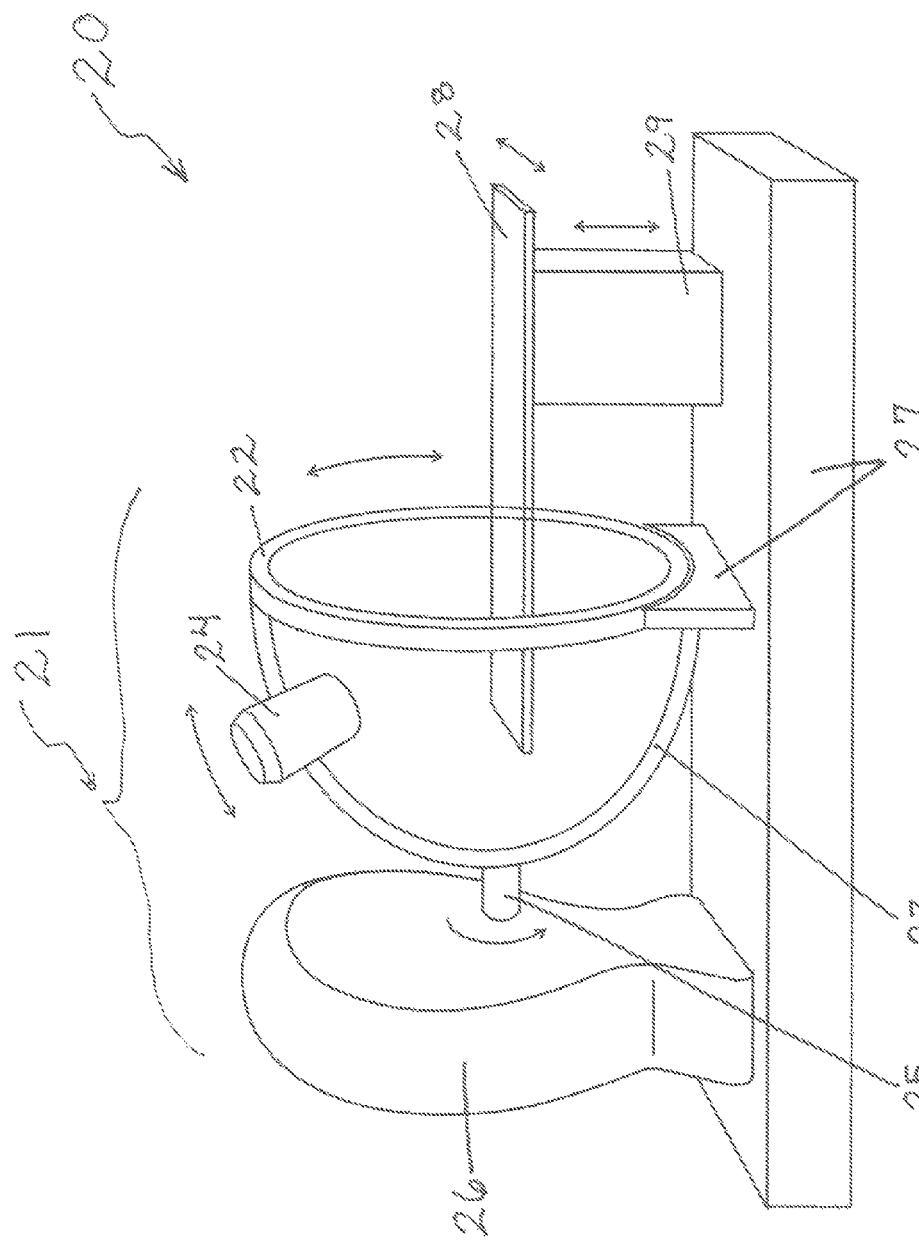

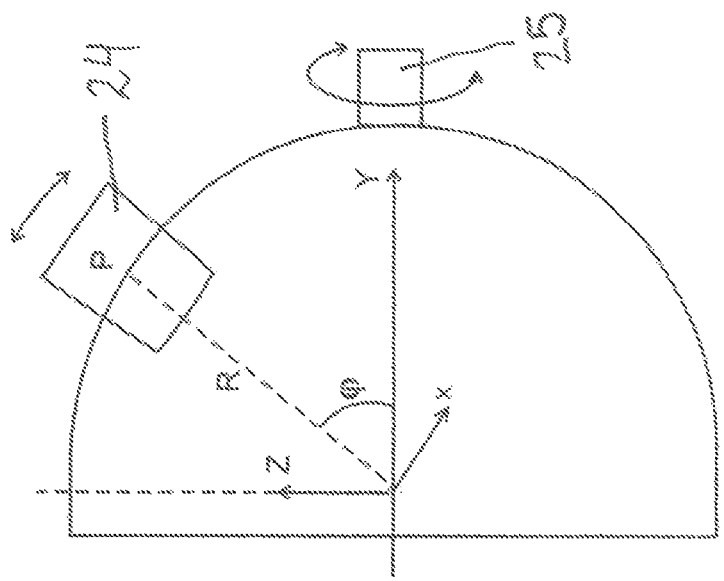
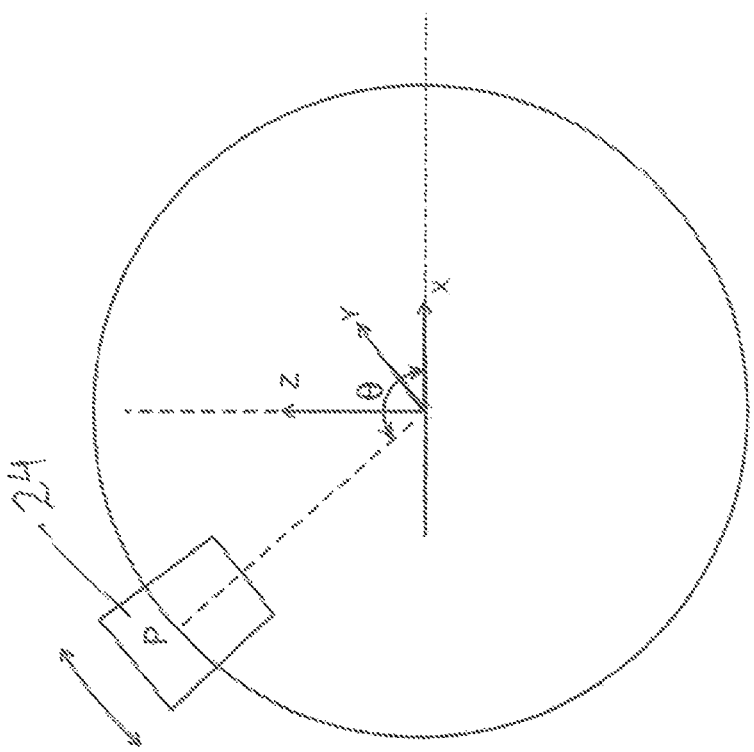
Fig. 3b
Fig. 3a

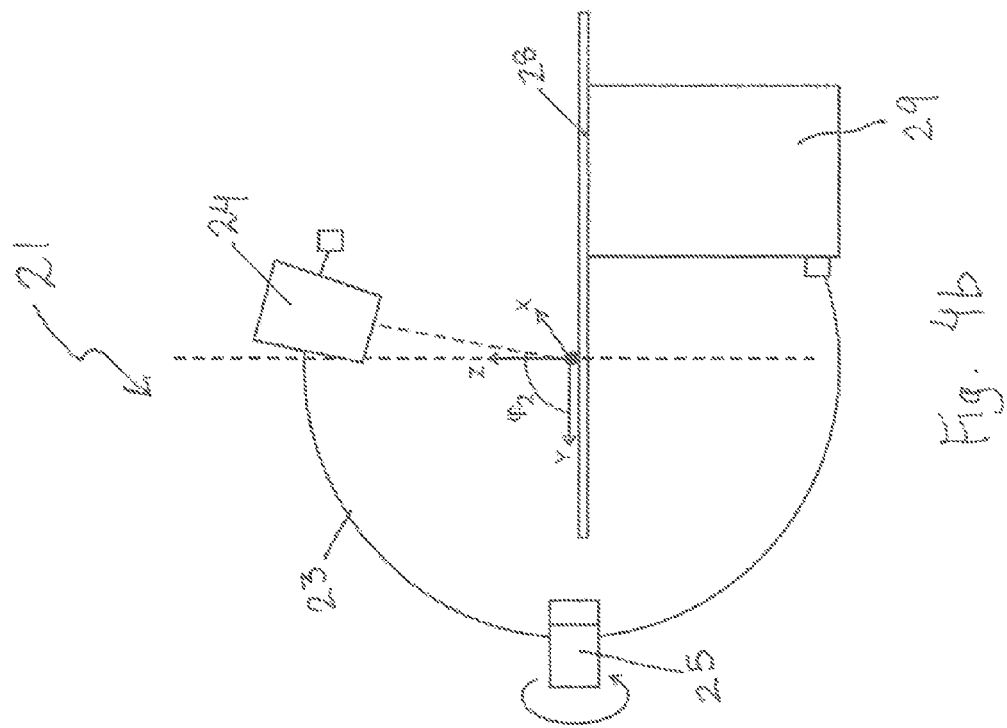
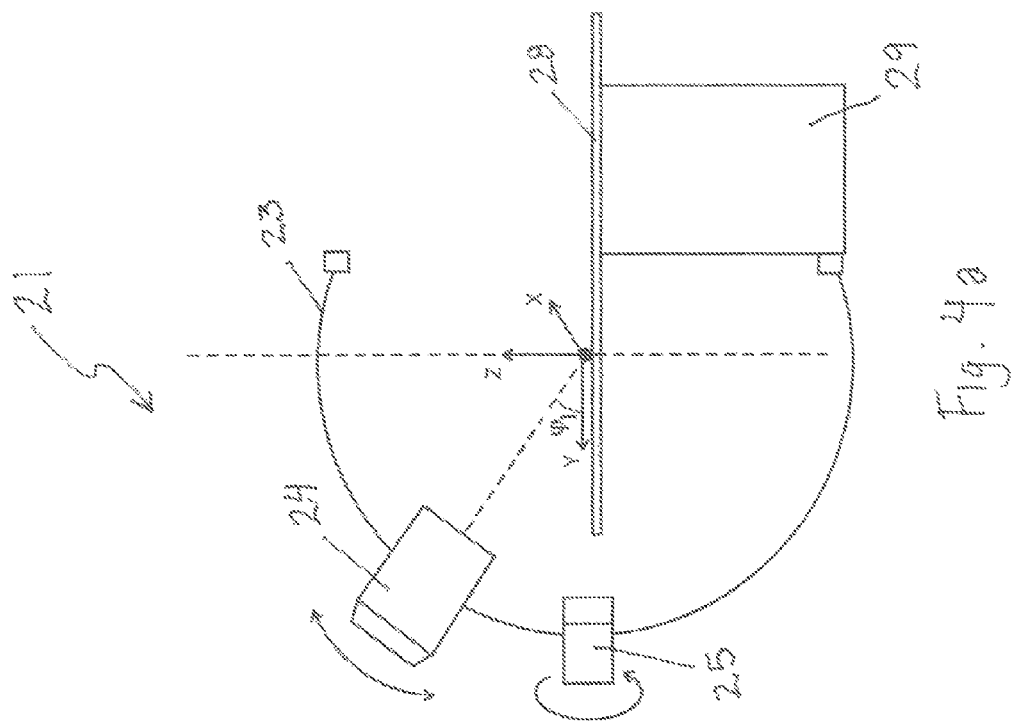

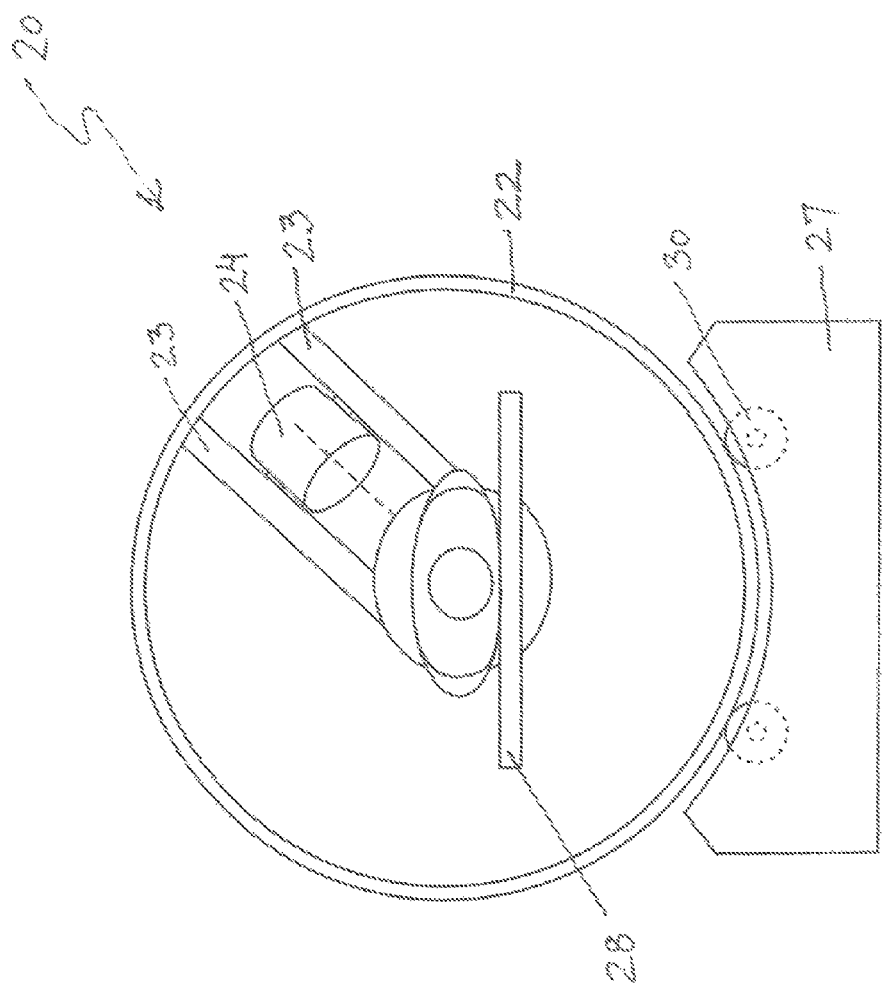

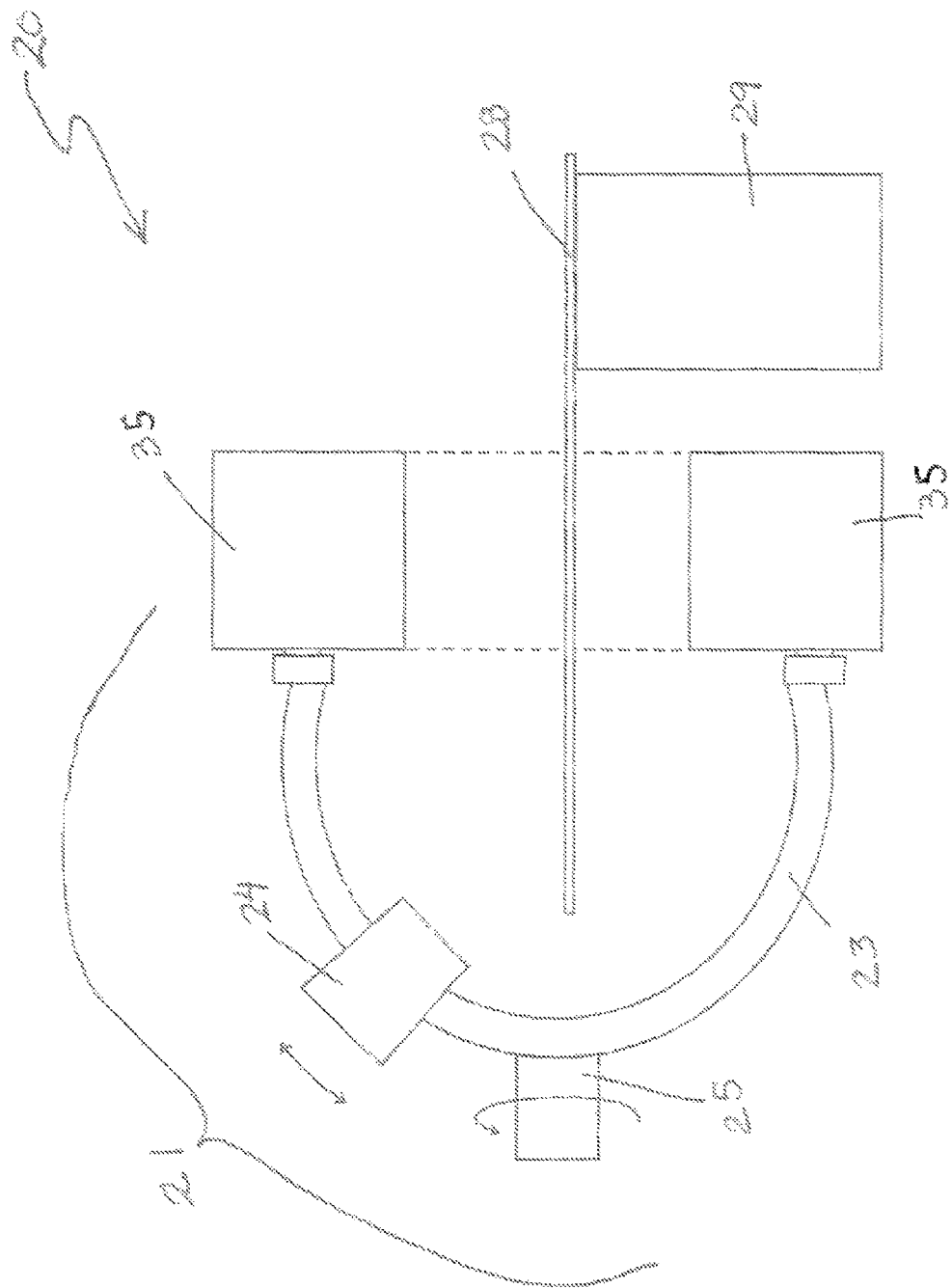

METHOD AND SYSTEM FOR STEREOTACTIC INTENSITY-MODULATED ARC THERAPY

TECHNICAL FIELD

The present disclosure relates to radiation therapy, in particular a method and a system for delivering focused radiation from outside of a patient's body to a target inside the patient. The method and the system aim intensity-modulated external radiation beams from a wide solid angle to deliver a focal dose of radiation to the target.

BACKGROUND

Radiation therapy is used to treat cancers and other conditions in patients. About half of all cancer patients receive some type of radiation therapy sometime during the course of their treatments. One commonly used form of radiation therapy is external beam radiation therapy. In external beam radiation therapy a high-energy, x-ray beam generated by a machine, usually a linear accelerator (linac), a gamma-ray beam emitted from an isotope, or charged particles generated from a particle accelerator is/are directed at a tumor or cancerous cells (i.e., the "target") inside the patient's body. While the radiation kills the cancerous cells, it also harms normal tissue and organs in the vicinity of the tumor/cancerous cells in the patient. Thus, the goal in radiation therapy is to deliver the required dose of radiation to the target volume, while minimizing the radiation dose to surrounding normal tissue that may cause complications and harm to the patient.

Before a patient is treated with radiation, a radiation treatment plan must be developed through a process called "treatment planning," which begins with simulation. During simulation, detailed imaging scans show the location of a patient's tumor and the normal areas around it. These scans are usually performed using computed tomography (CT), but they also can be performed using magnetic resonance imaging (MRI), x-rays or ultrasound.

The ability of radiation therapy to achieve the goal of tumor eradication and normal tissue sparing depends on the degrees of freedom provided by the radiation delivery machine and on the physics of dose deposition. These freedoms and physics principles are incorporated in the treatment planning process.

A common type of external-beam radiation therapy is called three-dimensional conformational radiation therapy (3D-CRT). 3D-CRT allows the radiation beams to be shaped from a limited number of fields to conform to the beam's eye-view of the target area.

Intensity-modulated radiation therapy (IMRT) provides more freedom than 3D-CRT by allowing the intensities of the radiation beams to vary within a radiation field in addition to field shaping. The goal of IMRT is to increase the radiation dose to the areas that need it and reduce radiation exposure to specific sensitive areas of surrounding normal tissue. The treatment planning system optimizes the beam intensity distribution to achieve maximally this goal. Compared with 3D-CRT, IMRT can reduce the risk of some side effects, such as damage to the salivary glands (which can cause dry mouth or xerostomia), when the head and neck are treated with radiation therapy (Veldeman et al., "Evidence behind use of intensity-modulated radiotherapy: A systematic review of comparative clinical studies," Lancet Oncology 9(4): 367-375 (2008); and Erratum in: Lancet Oncology 9(6): 513 (2008)).

Tomotherapy (Detorie, "Helical Tomotherapy: A new tool for radiation therapy," J. Amer. Coll. Radiol. 5(1): 63-66 (2008)) and intensity-modulated arc therapy (IMAT) (Yu, "Intensity modulated arc therapy using dynamic multi-leaf collimation: An alternative to Tomotherapy," Phys. Med. Biol. 40(9): 1435-1449 (1995)) are IMRT deliveries in rotational forms. In tomotherapy the patient is translated linearly as the source of radiation is making circular movements, thereby the relative motion of the radiation beam and the patient is a helix. Because the gantry on which the linear accelerator is mounted can only rotate in a single transverse plane, such "coplanar" rotational IMRT methods limit the range of beam directions available to create an optimal plan. Consequently, these techniques have not been shown to create significantly better dose distributions than IMRT with fixed beams.

3D-CRT and IMRT are typically delivered using a linear accelerator mounted on a C-arm gantry (as shown in FIG. 1) or a ring-like gantry, which is capable of only single plane rotation. These methods have limited ability to deliver high radiation doses in a single session or a few sessions without exceeding the tolerance of surrounding organs and tissues.

Stereotactic radiosurgery (SRS) and stereotactic body radiation therapy (SBRT) deliver one or more high doses of radiation to a small tumor (R. Timmerman and B. Kavanagh, "Stereotactic body radiation therapy," Curr. Probl. Cancer 29: 120-157 (2005)). SRS is commonly used for treating intracranial lesions and requires the use of a head frame or other device to immobilize the patient during treatment to ensure that the high dose of radiation is delivered accurately. The Gamma Knife (Bhatnagar et al., "First year experience with newly developed Leksell Gamma Knife Perfexion," J. Med. Phys. 34(3): 141-148 (2009)) is a dedicated SRS system for treating intracranial lesions. Gantry-based linear accelerator systems are also used for SRS. Both allow radiation beams to be incident on the target from directions outside the transverse plane. SBRT is used to treat tumors that lie outside the brain. SBRT is usually given in more than one treatment session. Methods of extending the Gamma Knife concept to the rest of the body are also proposed, such as with the GammaPod system for the treatment of breast cancer (Yu, et al., "GammaPod—A new device dedicated for stereotactic radiotherapy of breast cancer," Med. Phys. 40(5): 1703 (2013)) and the use of multiple sources mounted on an arc element that rotates (Pastyr et al., U.S. Pat. No. 6,259,762 B) for treating tumor sites other than in the brain. The principle of SRS and SBRT is geometric focusing of the beams to create a high dose within the target volume with a fast fall off of dose outside this volume. Focusing is achieved by aiming the radiation beams at the target from hundreds or thousands of directions. However, the ability to modulate the shape and intensity of these beams is limited. As such, SRS and SBRT have limited ability to spare surrounding tissues while maintaining a high and uniform dose within the target volume. For example, although the modern Gamma Knife has the ability to reach slightly below the base of the skull, attempts to use the Gamma Knife for treating complex targets in the head and neck region have had limited success. These regions (spinal cord, parotid glands, mandible, etc.) have complex geometric relationships to the target, and all have different radiation tolerances that need to be respected.

Techniques for delivering intensity modulated radiation from a large number of beam angles have been proposed. The CyberKnife system (J. Adler, "CyberKnife radiosurgery for brain and spinal tumors," International Congress Series 1247: 545-552 (2002)) employs a linear accelerator mounted on a robotic arm. It can deliver radiation from a large number of non-coplanar angles, but the practical number of beam angles is limited by the long treatment times associated with a large number of independent beams. Furthermore, the range of beam directions from the posterior hemisphere of the patient is restricted because of geometry constraints. Furthermore, the degree of beam modulation is limited by its collimator design.

Maurer and colleagues at Accuray, Inc., have proposed a number of alternative solutions using a fixed ring gantry, rather than a robotic arm (U.S. Pat. App. Pub. No. US 2011/0210261 A1; U.S. Pat. App. Pub. No. US 2011/0301449 A1; and U.S. Pat. App. Pub. No. US 2012/0189102 A1). While ring gantries are desirable for diagnostic imaging, where a single transverse plane or limited non-coplanar angles are used for the imaging beams, they are not ideal for treatment where a larger range of non-coplanar angles is desirable. For radiation treatment of most anatomical sites, the radiation beams are preferably directed to the target from one side of the patient's transverse axis, often from a large angle relative to this axis. For example, in treating intracranial lesions, most beams should be directed from the upper hemisphere (above the top of the patient's head) rather than from the lower hemisphere. Furthermore, it is often advantageous to use beams that are directed almost along the patient's longitudinal axis, demanding highly non-coplanar beams. In treating prostate cancer, it is generally preferable to direct beams from the lower body, rather than from the upper body, because it is better to have the beams go through less tissue and critical structures in the abdominal region. Flexible beam orientation ability throughout the lower body and some of the upper body is needed to achieve an optimal plan. The ring gantry systems proposed by Maurer and colleagues have limited ability to take advantage of such anatomical preferences or achieve highly non-coplanar beam directions.

Alternatively to exploring additional degrees of freedom, the physics of dose deposition can be altered by using different forms of radiation. External-beam radiation therapy can be delivered by proton beams and other charged particle beams. The charged particle beams differ from photon beams mainly in the way they deposit energy in living tissue.

Whereas photons deposit energy in small packets all along their path through tissue, including in regions both proximal to and distal to the target volume, protons deposit much of their energy at the end of their path (called the Bragg peak) and deposit less energy along the way. Proton energy deposition can thus be tailored to be largely within the target volume. The main limitation in providing these proton beam and charged particle treatment facilities is the extremely high cost.

Most existing linear accelerators or teletherapy machines can rotate around an axis by the rotation of the gantry on which the source of radiation is mounted. See, for example, FIG. 1, which is a drawing of a basic structure of a typical radiation treatment system in which a radiation-emitting head is mounted on a rotatable C-arm gantry. The locus of the radiation source forms a circle. During gantry rotation, the radiation beam is pointed at the rotational center, commonly referred to as the "isocenter." This design limits the beam directions to mostly planar angles and, therefore, limits the quality of treatment plans achievable with high-energy photon beams.

The present disclosure seeks to overcome the limitations of the attendant systems and methods currently available in the art by providing, among other things, a method to allow radiation beams to be focused from a broad solid angle by combined longitudinal and latitudinal rotations of the radiation source. In view of the foregoing, the present disclosure describes a method and a radiation delivery system to increase further the utility and clinical efficacy of photon-based treatment systems via increasing the degrees of freedom in beam delivery beyond that achievable with existing IMRT and SRS/SBRT systems. Specifically, this is achieved by allowing intensity-modulated photon beams to be delivered from a very large number of beam directions, including those which are highly non-coplanar. The solid angle range includes all longitudinal angles (about the patient's longitudinal axis) and a broad range of latitudinal angles. The methods and system combine, in a practical design, the geometric focusing of SRS/SBRT and intensity modulation of IMRT, thereby providing capabilities not attainable by either IMRT or SRS/SBRT alone. This and other objects and advantages, as well as inventive features, will become apparent from the detailed descriptions provided herein.

SUMMARY

A method of irradiating a target in a patient is provided. The method comprises directing a beam of radiation from an external source of radiation, such as at least one external source of radiation, at the target in the patient from numerous directions in a broad solid angle by longitudinally rotating the external source of radiation around a central axis and simultaneously or sequentially, in either order, latitudinally rotating the external source of radiation. Preferably, and even desirably, the external source of radiation is longitudinally rotated and latitudinally rotated concentrically around a common isocenter. The intensity of the beam of radiation, the shape of the aperture of the beam of radiation, or both the intensity and the shape of the aperture of the beam of radiation can be varied during irradiation throughout different points of longitudinal and/or latitudinal rotation or during maintenance of the external source of radiation at a single, static location. The speed of longitudinal rotation of the external source of radiation, the speed of latitudinal rotation of the external source of radiation, or both the speed of longitudinal rotation and the speed of latitudinal rotation of the external source of radiation can be varied. The external source of radiation can be longitudinally rotated and latitudinally rotated at a constant speed, whereupon the path of the external source of radiation, is a spherical helix. The breadth of the solid angle from within which at least one beam of radiation is directed can vary depending on the location of the target in the patient being irradiated. The method can further comprise continuously or discontinuously moving the patient during irradiation.

Further provided is a globe gantry for longitudinally and latitudinally rotating an external source of radiation, such as at least one external source of radiation, concentrically around an isocenter placed in a target to be irradiated. The globe gantry has a central axis intersecting the isocenter and comprises as components (i) a front opening ring with its origin on the central axis of the globe gantry, (ii) at least one arc-shaped, gantry support arm, which has a front end and a rear end and is part of a circle, (iii) an external source of radiation, such as at least one external source of radiation, which is mounted on at least one arc-shaped, gantry support arm, and optionally, a beam stopper, which is mounted on at least one arc-shaped, gantry support arm, and wherein the beam stopper is on the opposite side of the globe gantry from the external source of radiation, (iv) a rear rotational axle with an axis along the central axis of the globe gantry, (v) a support base, and (vi) a rear housing comprising a source of power, mechanisms for moving components of the globe gantry, and controllers for controlling the movement of the components of the globe gantry and the irradiation of the target in the patient. The front opening ring is attached to the front end of the at least one arc-shaped, gantry support arm. The rear rotational axle is attached to the rear end of the at least one arc-shaped, gantry support arm. The front opening ring and the rear rotational axle are supported by the support base and the rear housing. The front opening ring and the rear rotational axle can rotate around the central axis. The external source of radiation is a linear accelerator or a radioisotope teletherapy device. The globe gantry can rotate about the central axis at a variable speed. The external source of radiation can move along the length of the at least one arc-shaped, gantry support arm on which it is mounted at a variable speed. Alternatively, the external source of radiation is fixed on at least one arc-shaped, gantry support arm, and the arc-shaped, gantry support arm and the rear rotational axle are translated to cause the external source of radiation to rotate latitudinally. The globe gantry can comprise at least two arc-shaped, gantry support arms, which are separated by longitudinal angles of 180° or at least two pairs of adjacent arc-shaped, gantry support arms, which pairs are separated by longitudinal angles of 180°. The globe gantry can have a radius from about 40 cm to about 100 cm. The orientation of the central axis of the globe gantry can be changed from horizontal to substantially vertical or vertical, in which case the rear housing can rotate longitudinally and pivot between horizontal and vertical positions along with the globe gantry.

Still further provided is a system for irradiating a target in a patient. The system comprises (i) a globe gantry, (ii) a patient platform, (iii) a patient platform support, and, optionally, (iv) a shield. The patient platform is positioned along the central axis of the globe gantry and comprises a first end and a second end. The patient platform can be independently moved in either direction along the length of the patient platform or z-dimension, in either direction along the width of the patient platform or x-dimension, and/or in either direction above or below the patient platform or y-direction. The patient platform support supports the patient platform. The shield separates the patient from the rest of the system.

The system can further comprise (v) at least two straight support beams, (vi) an x-ray tube, and (vii) an x-ray detector array. The x-ray tube is mounted on at least one straight support beam on one side of the globe gantry. The x-ray detector array is mounted on at least one straight support beam on the opposite side of the globe gantry from the x-ray tube. The at least two straight support beams are parallel with the central axis of the globe gantry. The x-ray tube and the x-ray detector array are mounted at a longitudinal angle offset from the external source of radiation and, when present, the beam stopper, and can move along the lengths of the at least two straight support beams to which they are mounted. The x-ray detector array can be one-dimensional or multi-dimensional, such as two-dimensional. Alternatively, the system can further comprise (v) a computed tomography (CT) imaging system, a magnetic resonance imaging (MRI) system, or a positron emission tomography (PET)/computed tomography (CT) imaging system positioned adjacent to the front opening ring of the globe gantry, wherein the CT imaging system, the MRI system, or the PET/CT imaging system can provide on-board imaging guidance.

Even still further provided is a method of irradiating a target in a patient using the system. The method comprises creating a focal radiation dose by directing intensity-modulated beams of radiation from the external source of radiation, such as at least one external source of radiation, at the target in the patient in a treatment position from numerous directions in a broad solid angle by (a) longitudinally rotating the external source of radiation around a central axis and simultaneously or sequentially, in either order, latitudinally rotating the external source of radiation, or (b) longitudinally rotating the external source of radiation around a central axis and simultaneously or sequentially, in either order, latitudinally rotating the external source of radiation, while continuously or discontinuously moving the patient. When the system further comprises (v) either (a) at least one straight support beam, an x-ray tube, and an x-ray detector array, wherein the x-ray tube is mounted on at least one straight support beam on one side of the globe gantry, wherein the x-ray detector array is mounted on at least one straight support beam on the opposite side of the globe gantry from the x-ray tube, wherein the at least two straight support beams are parallel with the central axis of the globe gantry, and wherein the x-ray tube and the x-ray detector array are mounted at a longitudinal angle offset from the external source of radiation and, when present, the beam stopper, and can move along the lengths of the at least two straight support beams to which they are mounted, or (b) a CT imaging system, an MRI system, or a PET/CT imaging system positioned adjacent to the front opening ring of the globe gantry, the method further comprises acquiring a 3-D image set of the patient in the treatment position before irradiation, developing a treatment plan or adjusting an existing treatment plan based on the acquired set of images, in which case the focal dose of an intensity-modulated beam of radiation from the external source of radiation is directed at the target in the patient in accordance with the treatment plan.

BRIEF DESCRIPTION OF THE FIGURES

FIG. 2 is a drawing of a system 20 comprising (i) a globe gantry 21, which comprises a front opening ring 22, a gantry support arm 23, an external source of radiation 24 (e.g., at least one source of radiation), a rear rotational axle 25, a rear housing 26, and a support base 27, (ii) a patient platform 28, and a patient platform support 29.

FIG. 3(a) illustrates the coordinate system and the nomenclature associated with the front view of a globe gantry. The radius (R) is fixed. The location (P) of the source of radiation 24 is uniquely identified by its latitudinal angle ($\phi$) and its longitudinal angle ($\theta$), i.e., P($\phi$, $\theta$).

FIG. 3(b) illustrates the coordinate system and the nomenclature associated with a side view of a globe gantry, which includes a rear rotational axle 25. The radius (R) is fixed. The location (P) of the source of radiation 24 is uniquely identified by its latitudinal angle ($\phi$) and its longitudinal angle ($\theta$), i.e., P($\phi$, $\theta$).

FIG. 4(a) shows a partial side view of a radiation treatment system 20 when the external source of radiation 24 mounted on an arc-shaped, gantry support arm 23 is latitudinally rotated to near the rear (closed) end of the globe gantry 21, where the rear rotational axle 25 is located. Also shown are a patient platform 28 and a patient platform support 29.

FIG. 4(b) shows a partial side view of a radiation treatment system when the external source of radiation 24 mounted on an arc-shaped, gantry support arm 23 is latitudinally rotated to near the front (open) end of the globe gantry 21. Also shown are a patient platform 28 and a patient platform support 29.

FIG. 5 partially shows a radiation treatment system 20 when viewed from the front opening ring 22. Shown are the source of radiation 24 mounted on adjacent arc-shaped gantry support arms 23, a patient platform 28, and a support base 27 with rollers 30.

FIG. 12 illustrates how a 3-D imaging device 32 with a ring gantry can be abutted at the front ring of the globe gantry 21 of a system 20 to allow a patient to be imaged and treated while maintaining the same position on a patient platform. Shown are an arc-shaped, gantry support arm 23, an external source of radiation 24, a rear rotational axle 25, a patient platform 28, a patient platform support 29, and on-board 3-D imaging device 35.

DETAILED DESCRIPTION

Figure 1:
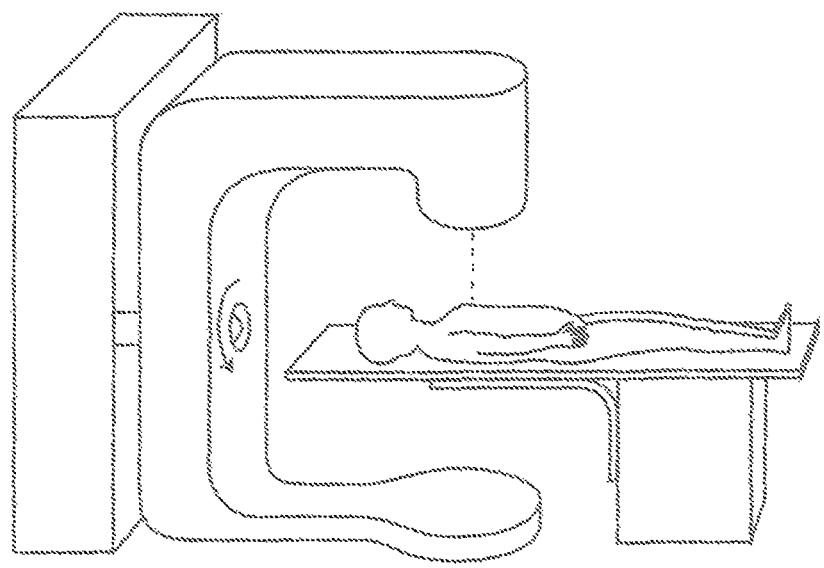
FIG. 1 is a drawing of a basic structure of a typical radiation treatment system in which a radiation-emitting head is mounted on a rotatable C-arm gantry.
Figure 6B:
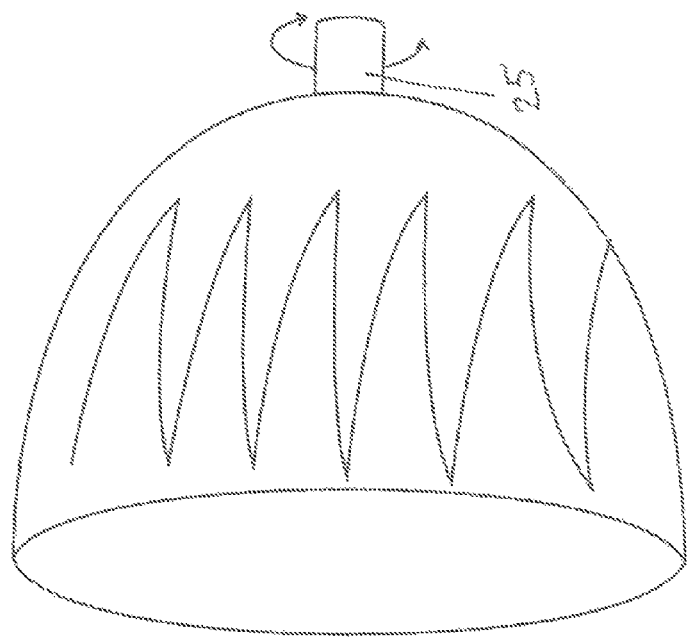
FIG. 6(b) illustrates the locus of the beam from the external source of radiation with slow longitudinal rotation and back and forth latitudinal rotation, whereby the locus of the beam from the external source of radiation forms a zigzag pattern on the surface of a sphere. Shown is the rear rotational axle 25.
Figure 6A:
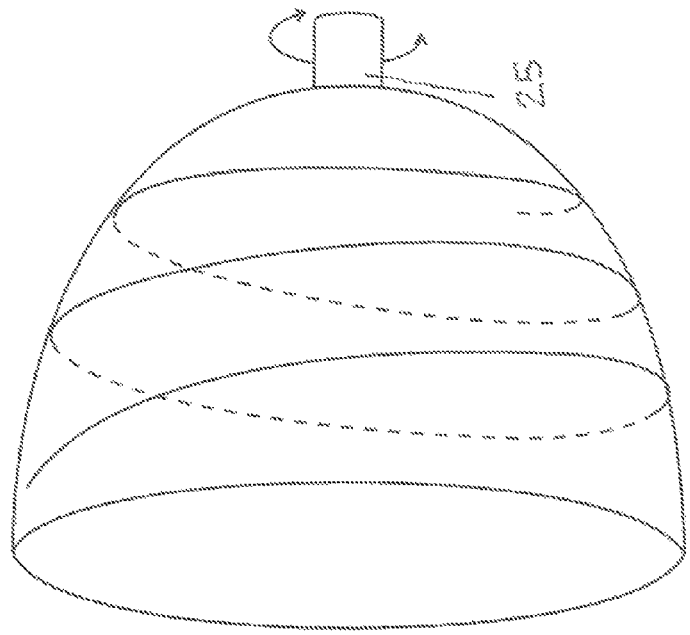
FIG. 6(a) illustrates the locus of the beam from the external source of radiation with constant speed of longitudinal and latitudinal rotation, whereby the locus of the beam from the external source of radiation forms a spherical helix. Shown is the rear rotational axle 25.

A method of irradiating a target in a patient is provided. The method comprises directing a beam of radiation from an external source of radiation, such as at least one external source of radiation, at the target in the patient from numerous directions (the directions can be so numerous as to be considered vast) in a broad solid angle. The external source of radiation is longitudinally rotated around the patient about an axis. Simultaneously with the longitudinal rotation or sequentially to the longitudinal rotation, in either order (i.e., either before or after), the external source of radiation can be rotated latitudinally via translation along a circular trajectory. Together, the longitudinal and latitudinal rotations of the external source of radiation in effect move the source of radiation in a trajectory that lies on the surface of a sphere. The range of latitudinal rotation is sufficient to allow large non-coplanar beam angles at one or both ends of the rotation range. Preferably, and even desirably, the central axis of the beam of radiation is focused on a fixed point in space throughout all rotations of the external source of radiation. This point is the "isocenter" or the intersection of the axes of longitudinal and latitudinal rotation. Thus, the external source of radiation is preferably, and even desirably, longitudinally rotated and latitudinally rotated concentrically around a common isocenter. The intensity of the beam of radiation, the shape of the aperture of the beam of radiation, or both the intensity and the shape of the aperture of the beam of radiation can be varied, such as during movement of the external source of radiation, i.e., during irradiation throughout different points of longitudinal and/or latitudinal rotation, or during maintenance of the external source of radiation at a single/static location. The speed of longitudinal rotation of the external source of radiation, the speed of latitudinal rotation of the external source of radiation, or both the speed of longitudinal rotation and the speed of latitudinal rotation of the external source of radiation can be varied. The breadth of the solid angle from within which the beam of radiation is directed can vary depending on the location of the target in the patient being irradiated. The breadth of the solid angle spanned by these rotations can vary depending on the location of the target in the patient being irradiated, allowing customization of the delivery for different locations. When the external source of radiation is longitudinally rotated and latitudinally rotated at a constant speed, the path of the external source of radiation is a spherical helix as shown in FIG. 6(a), which illustrates the locus of the external source of radiation with constant speed of longitudinal and latitudinal rotation, whereby the locus of the beam source forms a spherical helix. The longitudinal rotation and the latitudinal rotation can be performed in both directions. When the external source of radiation is longitudinally rotated slowly and latitudinally rotated constantly back and forth, the path of the external source of radiation is a zigzag as shown in FIG. 6(b), which illustrates the locus of the external source of radiation with slow longitudinal rotation and back and forth latitudinal rotation, whereby the locus of the beam source forms a zigzag pattern on the surface of a sphere. When the external source of radiation is longitudinally rotated back and forth and latitudinally rotated slowly, the path of the external source of radiation is connected segments of helices of opposite directions. The method can further comprise continuously or discontinuously moving the patient during irradiation, thereby allowing the radiation focal point to move dynamically within the target or be statically placed at one or more positions in and around the target. This method is referred to as stereotactic intensity-modulated arc therapy (SIMAT).

A globe gantry 21 for longitudinally and latitudinally rotating an external source of radiation concentrically around an isocenter placed in a target to be irradiated is also provided. The globe gantry 21 has a central axis intersecting the isocenter and can rotate the external source of radiation 24 throughout a 360° range about a longitudinal axis. This movement is referred to herein as "longitudinal rotation," and the external source of radiation is said to "rotate longitudinally" or "longitudinally rotate" or to be "longitudinally rotated" when it rotates around the longitudinal axis. Preferably, and even desirably, the globe gantry 21 can rotate in either direction, i.e., clockwise and counterclockwise. Also preferably, and even desirably, the globe gantry 21 can rotate at a variable speed. The globe gantry 21 comprises the following components: (i) a front opening ring 22 with its origin on the central axis of the globe gantry 21, (ii) at least one arc-shaped, gantry support arm 23, which has a front end and a rear end and is part of a circle, (iii) an external source of radiation (24; also referred to as a "radiation-generating device," a "radiation-emitting device," and a "radiation head"), which is mounted on at least one arc-shaped, gantry support arm 23, and, optionally, a beam stopper, which is mounted on at least one arc-shaped, gantry support arm 23, and wherein the beam stopper is on the opposite side of the globe gantry 21 from the external source of radiation 24, (iv) a rear rotational axle 25 with an axis along the central axis of the globe gantry 21, (v) a support base 27, and (vi) a rear housing 26 comprising a source of power, mechanisms for moving components of the globe gantry 21, and controllers for controlling the movement of the components of the globe gantry 21 and the irradiation of the target in the patient. The front opening ring 22 is attached to the front end of the at least one arc-shaped, gantry support arm 23. Preferably, the front opening ring 22 is attached to the front ends of at least two arc-shaped, gantry support arms 23, which are separated by longitudinal angles of 180°, or at least two pairs of adjacent arc-shaped, gantry support arms 23, which pairs are separated by longitudinal angles of 180°. The curvature of the arc-shaped, gantry support arm(s) 23 enables movement of the external source of radiation 24 along a circular path with a fixed origin, i.e., the isocenter, that lies on the rotational axis of the globe gantry 21 and, when present, the beam stopper. The front opening ring 22 desirably provides support and rigidity. The front opening ring 22 is supported by rollers 30, bearings, or the like set on the support base 27, such that the front opening ring 22 can freely rotate on the support base 27. The rear, rotational axle 25 is attached to the rear end of the at least one arc-shaped, gantry support arm 23 and facilitates longitudinal rotation of the globe gantry 21. Longitudinal rotation also can be achieved by driving the front opening ring 22. When there are at least two arc-shaped, gantry support arms 23, preferably the rotational axle is attached to the rear ends of the at least two arc-shaped, gantry support arms 23, and the two arc-shaped, gantry support arms 23 form part of a circle. With such a configuration, the arc-shaped, gantry support arms 23 are affixed to, and extend outwardly and forward from, the rear rotational axle 25. The front opening ring 22 and the rear rotational axle 25 are supported by the support base 27 and the rear housing 26. The front opening ring 22 and the rear rotational axle 25 can rotate around the central axis. Such a configuration, when rotated about the central axis, occupies a space resembling part or all of a sphere or a globe. In this regard, the globe gantry can be slightly more or less hemispheric.

Driving mechanisms can be attached at any suitable place(s) on the globe gantry. For example, driving mechanisms can be attached to the rear, rotational axle 25 and/or the front, opening ring 22.

Preferably, a slip ring is used to supply the electricity from the rear housing 26 to the external source of radiation 24, the signals from the sensors, and the communication signals from the control system to the source of radiation 24, including the collimation system. The slip ring also may be used to transfer cooling water to and from the rotating globe gantry 21. Slip-ring technology is not necessary when the globe gantry 21 is rotated back and forth with a maximum range of rotation in a single direction that does not significantly exceed 10 turns (i.e., 3600°).

Preferably, the globe gantry 21 has a mechanism to prevent unintended rotation in the event that there is a loss of power and the weight on the globe gantry 21 is not balanced around the globe. Such a mechanism serves to protect the patient and the globe gantry 21, as well as a system 20 comprising the globe gantry.

The globe gantry can have any suitable radius. Desirably, the globe gantry 21 has a radius that is large enough for the intended application. For treatment of tumors in the torso of a patient, the diameter of the front opening ring should be sufficient to allow a patient, in particular a human patient, to be placed in the interior space of the globe gantry 21 and, optionally moved in three dimensions within the interior space of the globe gantry 21. Preferably, the globe gantry 21 has a radius from about 40 cm to about 100 cm, such as from about 40 cm to about 90 cm, from about 40 cm to about 80 cm, from about 40 cm to about 70 cm, from about 40 cm to about 60 cm, from about 40 cm to about 50 cm, from about 50 cm to about 100 cm, from about 60 cm to about 100 cm, from about 70 cm to about 100 cm, from about 80 cm to about 100 cm, or from about 90 cm to about 100 cm.

The orientation of the central axis of the globe gantry 21 can be changed. For example, the orientation of the central axis can be changed from horizontal to substantially vertical or vertical, in which case the rear housing can rotate longitudinally and pivot between horizontal and vertical positions along with the globe gantry. A substantially horizontal or horizontal orientation can allow, for example, a patient's head and a patient's body supported by a patient platform 28 to be placed inside the globe gantry. When the central axis is oriented substantially vertically or vertically with the front ring 22 facing upwards, the patient can lay prone on a patient platform 28 in the globe gantry. Preferably, the patient platform 28 comprises an opening for a breast of a female patient to be placed inside the globe gantry 21, in which case the breast is pendent in the opening in the patient platform 28.

The external source of radiation 24, such as at least one external source of radiation 24, is preferably mounted on a pair of adjacent arc-shaped, gantry support arms 23. Mounting the external source of radiation 24 on a pair of adjacent arc-shaped, gantry support arms 23, as opposed to a single, arc-shaped, gantry support arm 23, can provide greater stability and better control of the external source of radiation 24. Preferably, and even desirably, the external source of radiation 24 can move or translate along the length(s) of the arc-shaped, gantry support arm(s) 23 to which it is attached. Also preferably, and even desirably, the external source of radiation 24 can move or translate along the length(s) of the arc-shaped, gantry support arm(s) 23 to which it is attached at a constant speed or a variable speed, with a variable speed being preferred. Because the arc-shaped, gantry support arms 23 are part of a circle on the surface of a globe, this movement is referred to herein as "latitudinal rotation," and the external source of radiation is said to "rotate latitudinally" or "latitudinally rotate" or to be "latitudinally rotated" when it moves/translates along the length(s) of the gantry support arm(s) 23. The position of the external source of radiation 24 can be uniquely identified by its longitudinal and latitudinal angles. The coordinate system and nomenclature associated with a globe gantry 21 used in a system 20 for planning SIMAT treatment is illustrated in FIGS. 3(a) and 3(b). FIG. 3(a) illustrates the coordinate system and the nomenclature associated with the front view of a globe gantry 21. The radius (R) is fixed. The location (P) of the source of radiation 24 is uniquely identified by its latitudinal angle ($\phi$) and its longitudinal angle ($\theta$), i.e., P($\phi$, $\theta$). FIG. 3(b) illustrates the coordinate system and the nomenclature associated with a side view of a globe gantry 21. The source of radiation 24 can be at different latitudinal and longitudinal angles, at all times pointing to the isocenter. Rotation of the globe gantry 21 changes the longitudinal angle of the beam of radiation. The latitudinal rotation of the external source of radiation 24 varies the latitudinal angle of the beam of radiation.

The speed of longitudinal rotation and the speed of latitudinal rotation of the external source of radiation 24 can be, but need not be, and preferably are not, constant. The trajectory of the source of radiation 24 under such conditions is not a perfect spherical helix. Moreover, the longitudinal and latitudinal rotation of the external source of radiation 24 is generally not mono-directional, i.e., it can be rotated back and forth in both directions as needed, and each movement in one direction can be complete or incomplete, i.e., longitudinal rotations that are not necessarily throughout 360 degrees and latitudinal rotations that do not necessarily involve translation of the source along the entire length(s) of the arc-shaped, gantry support arm(s) 23. In this regard, the starting and stopping positions along the arc-shaped, gantry support arm(s) 23 can vary with the longitudinal angle of the location of the external source of radiation 24. The axis of the radiation beam always points to the origin of the sphere.

The range of the latitudinal angles is not symmetrical about the plane through the isocenter and perpendicular to the longitudinal axis of the globe gantry 21. For the situation where the longitudinal axis is oriented along the length of the patient and patient platform 28, this asymmetry of latitudinal rotation is about the vertical plane through the isocenter and transverse to the patient platform 28. In the field of radiation oncology, radiation beams with their axes coplanar with a transverse plane of a patient platform (or patient) 28 are referred to as "coplanar beams," whereas radiation beams angled obliquely from above or below the transverse plane of the patient platform (or patient) 28 are referred to as "non-coplanar beams." For the situation where the longitudinal axis is oriented perpendicularly to the patient and patient platform (28; as in FIG. 8), the asymmetry of latitudinal rotation is about the horizontal plane through the isocenter. The beam of radiation has a smaller maximum obliquity at the front open ring 22 end as compared to the rear closed end by the rear, rotational axle 25. This configuration provides the largest possible solid angle without constricting the opening of the treatment space. This arrangement is desirable because it allows the treatment space to be sufficiently large to accommodate patients of varying size, and it enables irradiation of a wide range of target sites within a patient.

An alternative mechanical system for moving at least one source of radiation in a sphere, while keeping the beam focused on a fixed location in space, is also provided. In this alternative mechanism, the radiation head 24 is fixed on the arc-shaped, gantry support arm 23, and the arc-shaped, gantry support arm 23 and the rear, rotational axle 25 are translated, causing the external source of radiation 24 to rotate latitudinally.

The globe gantry 21 can be made from any suitable material in accordance with methods known in the art. Preferably, the globe gantry 21 is made from a strong material that is durable and lightweight. Desirably, the globe gantry 21 can be easily rotated, and the support beams can support attachments, such as an external source of radiation 24, a beam stopper, and the like, and can withstand repeated movement of the external source of radiation 24 and, when present, the beam stopper along their lengths in both directions (i.e., the directions of latitudinal rotation). An example of a preferred material is metal.

A system 20 for irradiating a target in a patient is also provided. The system 20 comprises the following components: (i) a globe gantry 21 as described herein, (ii) a patient platform 28, which is positioned along the central axis of the globe gantry 21 and which comprises a first end and a second end, (iii) a patient platform support 29, which supports the patient platform 28, and, optionally, (iv) a shield, which separates the patient from the rest of the system.

FIG. 2 is a drawing of a system 20 comprising a globe gantry 21. Rather than having the source of radiation fixed on a C-arm gantry, the arms of the globe gantry form part of a circle, and the external source of radiation 24 can latitudinally rotate along an arm of the gantry. When the gantry is longitudinally rotated and the external source of radiation 24 is rotated latitudinally along the arc-shaped support arm 23, the locus of the movement of the source of radiation is generally part of the surface of a sphere, rather than a circle. During such movement, the radiation beam provided by (e.g., emitted by or generated by) the external source of radiation 24 points to the origin of the sphere, the radiation intensity can be varied, and the aperture of the radiation field can be changed. Thereby, two of the widely adopted techniques for delivering radiation doses to conform to the shape of the target in a patient—intensity modulation and geometric focusing—can be combined. During the movement of the radiation beams, the patient can also be moved, allowing the rotational isocenter of the radiation beam to scan through the target in the patient analogously to three-dimensional printing or painting, thereby covering an irregularly shaped target (e.g., tumor) with the desired dose patterns.

FIG. 4(a) shows a side view of a radiation treatment system 20 when the at least one source of radiation 24 mounted on an arc-shaped, gantry support arm 23 is latitudinally rotated to near the rear (closed) end of the globe gantry 21. Because it is rarely desirable to direct the radiation beam towards the vertex of a patient's head or the bottom of a patient's feet, the latitudinal angle ($\phi$) practically need not be smaller than about 30°.

FIG. 4(b) shows a side view of a radiation treatment system 20 when the at least one source of radiation 24 mounted on an arc-shaped, gantry support arm 23 is latitudinally rotated to near the front (open) end of the globe gantry 21. There is more latitudinal angular range on the rear side than on the front side of the transverse plane across the isocenter, thereby allowing large, non-coplanar beam angles from the closed end of the gantry. In most cases, it is not necessary to have the radiation beams arranged symmetrically about the transverse plane through the isocenter. Therefore, the latitudinal angle (φ) practically need not be greater than about 120°.

FIG. 5 shows a radiation treatment system 20 when viewed from the front open ring 22. The globe gantry 21 can rotate smoothly, for example, on ball bearings in the support base 27. The radiation head 24 is rotated to a longitudinal angle (θ).

The external source of radiation 24 can be any suitable source of radiation. Preferably, and even desirably, the external source of radiation 24 is a self-contained radiation machine. Preferred examples of sources of radiation 24 include, but are not limited to, a linear accelerator and a radioisotope teletherapy device, such as a cobalt-60 teletherapy head. When the external source of radiation 24 is a linear accelerator, the microwave power generator and/or amplifier for electron acceleration, the accelerator waveguide, as well as other necessary components for shaping the radiation field, are preferably all enclosed in a single, unitary container. The high-voltage pulse generation modulator and other control circuitry can be placed inside the support base. In this arrangement, the electrical power required to energize a radiation-generating head and/or the cold water required to cool the acceleration guide and the target are preferably connected through a slip-ring mechanism. The external source of radiation 24 comprises the necessary shielding around the radiation source, a primary collimator, and a radiation aperture-shaping device, such as a multi-leaf collimator. The beam of radiation is collimated with the primary collimator. In a preferred embodiment, a multi-leaf collimator shapes the field of radiation dynamically during irradiation and movement. The power and cooling needed for the source of radiation can be supplied through a slip-ring connector.

Preferably, and even desirably, the external source of radiation 24 is coupled with a beam stopper, which is mounted on at least one arc-shaped, gantry support arm 23 on the opposite side of the globe gantry 21 from the external source of radiation 24. The beam stopper is a radiation-shielding plate that attenuates the exit beam from the patient. Examples of suitable beam stoppers are known in the art and include, for example, a high-density material, such as lead encased in steel or tungsten alloy. In addition to shielding radiation from the external source of radiation 24, the beam stopper can act as a counter-weight to the external source of radiation 24. The beam stopper reduces the shielding requirements of the treatment room. Preferably, and even desirably, the beam stopper can move along the length(s) of the arc-shaped, gantry support arm(s) 23 to which it is mounted and moves in the opposite direction of the external source of radiation 24. Since the external source of radiation 24 preferably, and even desirably, moves at a constant speed or a variable speed, with a variable speed being preferred, it is also preferred, and even desired, for the beam stopper to move at a constant speed or a variable speed accordingly. The ability of the beam stopper to move helps to minimize the size of the beam stopper required to block the exit of the radiation beam from the patient. As the radiation head moves from a positive latitudinal angle to a negative latitudinal angle, the beam stopper moves from a negative latitudinal angle to a positive latitudinal angle (and vice versa) so as to maintain its function of blocking the exit beam from the patient. Because the globe gantry 21 is latitudinally asymmetric, the beam stopper should be mounted in such a way that it can be latitudinally rotated passing the front opening ring 22. Alternatively, the beam stopper can be a fixed, arc-shaped plate that connects the front opening ring 22 to the rear, rotational axle 25, serving both as a shield of the radiation exiting from the patient and as structural support providing rigidity to the globe gantry 21. The width and the circular arc length of the shielding plate in this alternative embodiment are sufficient for shielding the exit beam when the radiation head is at any possible location on the globe gantry.

A preferred patient platform 28 is a table or a couch. Preferably, and even desirably, the patient platform 28 can be independently moved in various directions. For example, the patient platform 28 can be moved in either direction along the length of the patient platform 28 or z-dimension, in either direction along the width of the patient platform 28 or x-dimension, and/or in either direction above or below the patient platform 28 or y-direction. Independent movement of the patient platform 28 in three directions can be driven by at least three motors, for example. Depending on the location of the target in the patient to be irradiated, it can be desirable to have the patient lie on the patient platform 28 with his/her head at the first end or the second end.

Any suitable patient platform support 29 can be used to support the patient platform. An example of a suitable patient platform support 29 is a pedestal, such as a pedestal in front of the front opening ring 22, such that the patient platform 28 is suspended inside the globe gantry 21.

The support base 27 can be any suitable supportive structure, such as a solid platform, that stabilizes the front opening ring 22, the rear, rotational axle 25, and, if desired, the patient platform 28, for better geometric stability.

The shield, which separates the patient from the rest of the system 20, can be any suitable shield as known in the art. Preferably, the shield is thin and protective and separates the patient from the globe gantry 21, the external source of radiation 24, and other moving parts, which are mounted on or adjacent to the globe gantry 21. The shield can have any suitable shape, such as a hemispherical shape, and can be established around the patient prior to treatment. The shield can be transparent, translucent, or opaque. A patient may prefer a transparent shield when a target in the torso region is being irradiated so as not to feel enclosed. In contrast, a patient may prefer an opaque shield when a target in the head/neck region is being irradiated so as to hide the movement of the source of radiation 24 near the patient's face. The shield can be made from any suitable material. Preferably, the shield is shatterproof and radiation-tolerant. In this regard, a plastic, such as polycarbonate, can be preferred. The shield should be as thin as possible to minimize scatter radiation, which can increase the radiation dose to the skin. Preferably, the thickness of the shield is about 1 mm or less. The use of a thin shield and a broad solid angle to focus the beam of radiation helps to keep the radiation dose to the skin as minimal as possible.

Figure 11A:
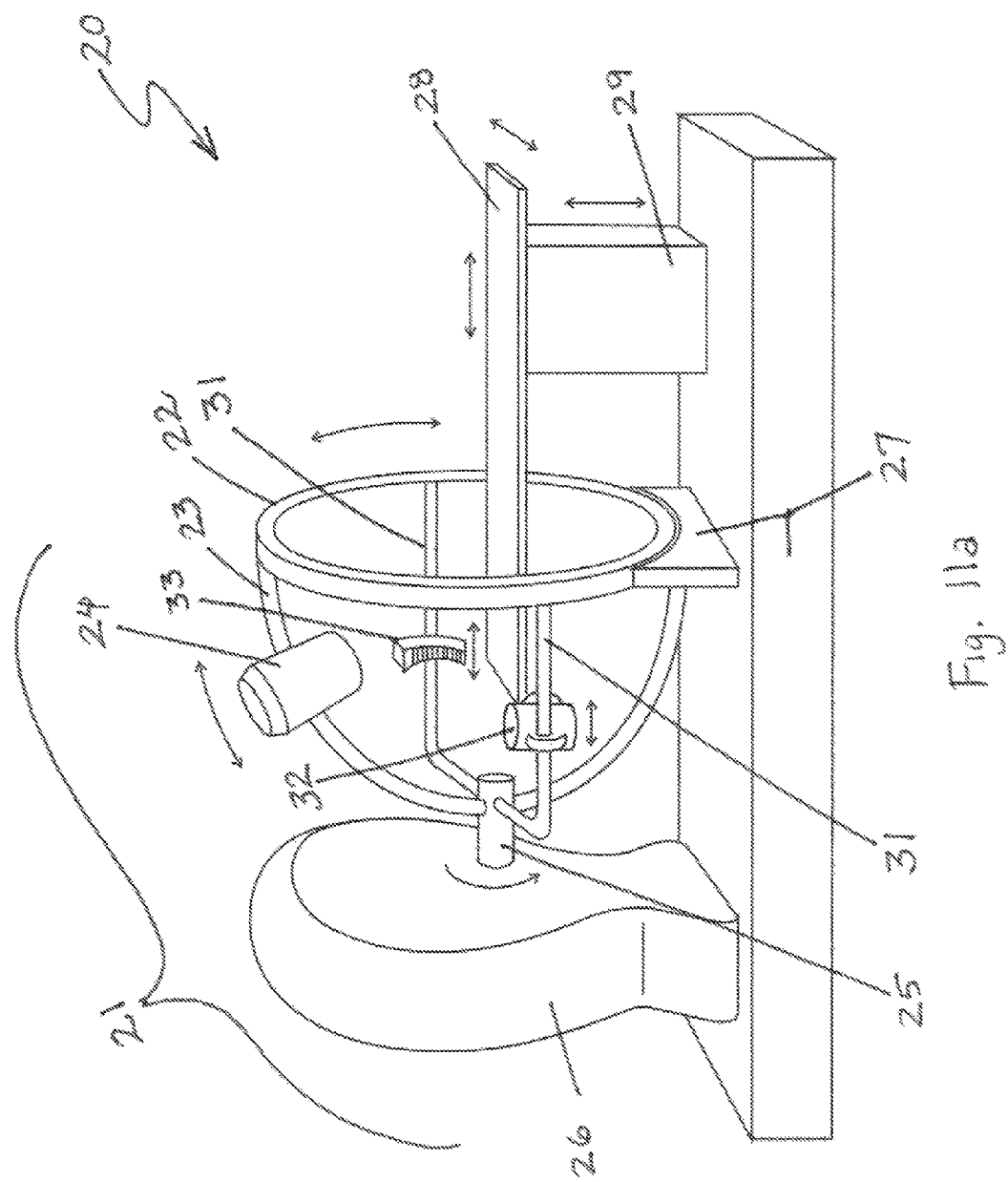
FIG. 11(a) shows a side view of a system 20 in which straight support beams 31 are attached to the globe gantry 21 to facilitate on-board imaging, such as 2-D x-ray or 3-D CT imaging. Shown are a front opening ring 22, arc-shaped, gantry support arms 23, an external source of radiation 24, a rear rotational axle 25, a rear housing 26, a support base 27, a patient platform 28, a patient platform support 29, and on-board imaging with an x-ray tube 32 and an x-ray detector array 33.
Figure 11B:
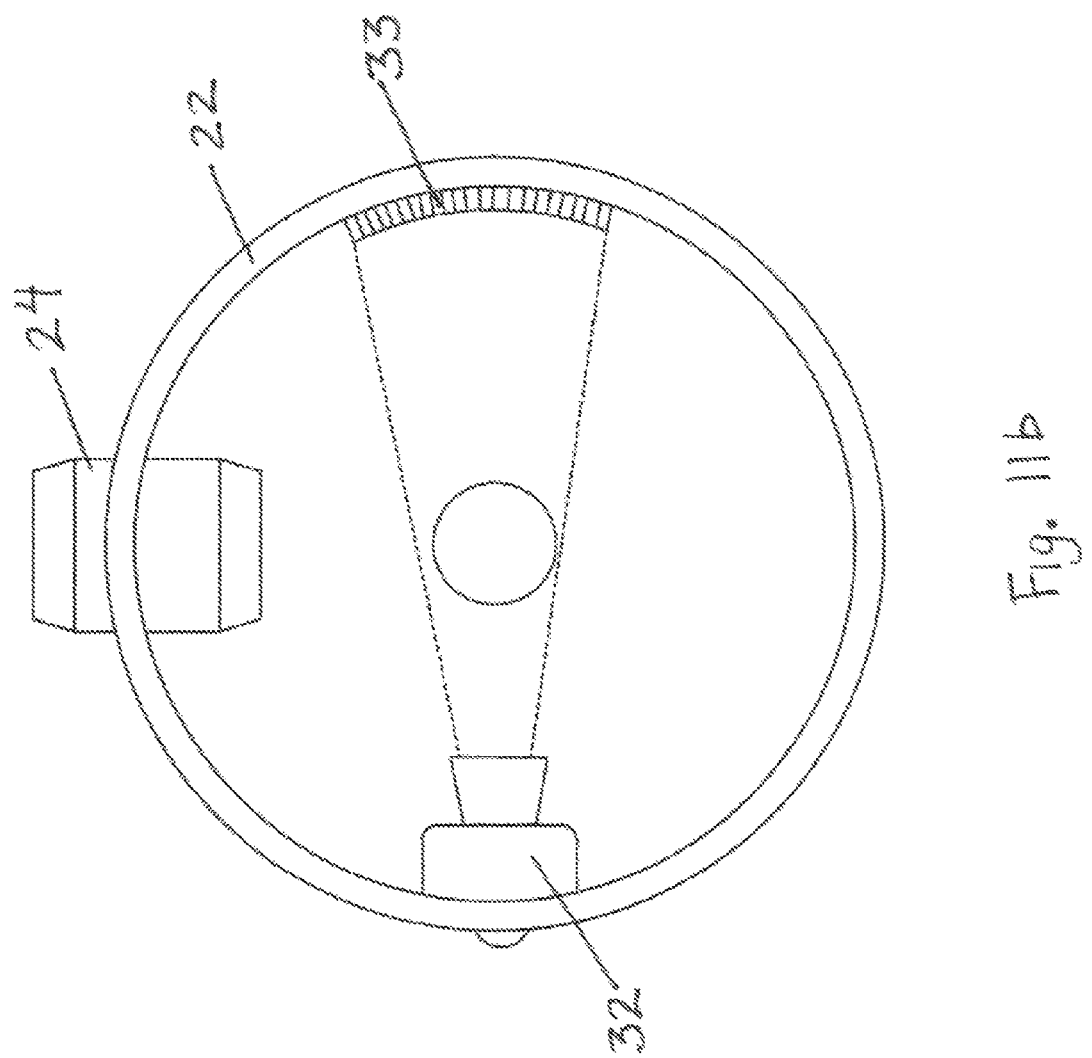
FIG. 11(b) shows the view from the front ring of the globe gantry 21 of a system 20 in which straight support beams 31 are attached to the globe gantry 21 to facilitate on-board imaging, such as 2-D x-ray or 3-D CT imaging. Shown are a front opening ring 22, an external source of radiation 24, and on-board imaging with an x-ray tube 32 and an x-ray detector array 33.

The system 20 can further comprise the following components: (v) at least two straight support beams 31, (vi) an x-ray tube 32, and (vii) an x-ray detector array 33 as shown in FIGS. 11(a) and 11(b). FIG. 11(a) shows a side view of a system 20 in which straight support beams 31 are attached to the globe gantry 21 to facilitate on-board imaging, such as 2-D x-ray or 3-D CT imaging, wherein on-board imaging with an x-ray tube 32 and an x-ray detector array 33 is shown. FIG. 11(b) shows the view from the front ring 22 of the globe gantry 21 of a system 20 in which straight support beams 31 are attached to the globe gantry 21 to facilitate on-board imaging with an on-board imaging device 32, such as 2-D x-ray or 3-D CT imaging, wherein on-board imaging with an x-ray tube 32 and an x-ray detector array 33 is shown. The x-ray tube 32 is mounted on at least one straight support beam 31 on one side of the globe gantry 21. The x-ray detector array 33 is mounted on at least one straight support beam 31 on the opposite side of the globe gantry 21 from the x-ray tube. Thus, the x-ray tube 32 and the x-ray detector array 33 are mounted on support beams that are separate from those that support the external source of radiation and the beam stopper. The at least two straight support beams 31 are parallel with the central axis of the globe gantry 21. The x-ray tube 32 and the x-ray detector array 33 are mounted at a longitudinal angle offset (e.g., about 90°) from the external source of radiation 24 and, when present, a beam stopper, so that the movements of the external source of radiation 24 and, when present, the beam stopper, do not interfere with the movements of the imaging apparatus, and can move along the lengths of the at least two straight support beams 31 to which they are mounted. Preferably, and even desirably, the x-ray tube 32 and the x-ray detector 33 can translate in synchrony along the straight support beams 31 for imaging an area of interest, such as an area comprising a target to be irradiated, in a patient before, during, or after treatment. The x-ray tube 32 and x-ray detector array 33 can translate independently of the external source of radiation 24 and, when present, the beam stopper. In this arrangement, imaging and treatment can be performed simultaneously or sequentially. The x-ray detector array 33 is one-dimensional or multi-dimensional, such as two-dimensional.

Alternatively to at least two straight support beams 31, an x-ray tube 32, and an x-ray detector array 33, the system 20 can further comprise the following component: (v) a computed tomography (CT) imaging system, a magnetic resonance imaging (MRI) system, or a positron emission tomography (PET)/computed tomography (CT) imaging system positioned adjacent to the front opening ring 22 of the globe gantry 21 as shown in FIG. 12, which illustrates how a three-dimensional imaging device on a ring gantry can be abutted at the front ring 22 of the globe gantry 21 of a system 20 to allow a patient to be imaged and treated while maintaining the same position on a patient platform. The CT imaging system, the MRI system, or the PET/CT imaging system can provide on-board imaging guidance 35.

Desirably, the same patient platform (28 or 28 and 29) is used for imaging and irradiation to minimize geometric uncertainty. Therefore, the patient can be imaged and treated without moving the patient from a fixed position on the patient platform (28 or 28 and 29).

A method of irradiating a target in a patient using a system 20 as described herein is also provided. The method comprises creating a focal radiation dose by directing intensity-modulated beams of radiation from an external source of radiation 24 at the target in the patient from numerous directions in a broad solid angle by (a) longitudinally rotating the external source of radiation 24, such as at least one external source of radiation, around a central axis and simultaneously or sequentially, in either order, latitudinally rotating the external source of radiation 24, such as at least one external source of radiation, or (b) longitudinally rotating the external source of radiation 24, such as at least one external source of radiation, around a central axis and simultaneously or sequentially, in either order, latitudinally rotating the external source of radiation 24, such as at least one external source of radiation, while continuously or discontinuously moving the patient.

The speed of the globe gantry 21 is from about 1 rpm to about 4 rpm, which is much slower than that of a CT scanner. Preferably, and even desirably, the speed of the rotation of the globe gantry 21 is not constant. The speed of latitudinal rotation of the source of radiation 24 also can be variable so that the radiation beam can stay longer at preferred orientations and avoid undesirable orientations. During treatment, the source of radiation 24 can be latitudinally rotated back and forth, with each range of latitudinal rotation being different. Therefore, the latitudinal offset angle from the transverse plane through the isocenter can be larger on one side of the patient's body than on the other side. When a linear accelerator is used as the source of radiation 24, the radiation output rate also can vary as the source of radiation 24 is longitudinally and latitudinally rotated by means currently used in the art, such as changing the pulse width and the intervals between the pulses.

In the method the system 20 can further comprise (v) either (a) at least one straight support beam 31, an x-ray tube 32, and an x-ray detector array 33, wherein the x-ray tube 32 is mounted on at least one straight support beam 31 on one side of the globe gantry 21, wherein the x-ray detector array 33 is mounted on at least one straight support beam 31 on the opposite side of the globe gantry 21 from the x-ray tube 32, wherein the at least two straight support beams 31 are parallel with the central axis of the globe gantry 21, and wherein the x-ray tube 32 and the x-ray detector array 33 are mounted at a longitudinal angle offset from the external source of radiation 24 and, when present, the beam stopper, and can move along the lengths of the at least two straight support beams 31 to which they are mounted, or (b) a CT imaging system, an MRI system, or a PET/CT imaging system positioned adjacent to the front opening ring 22 of the globe gantry 21, wherein the CT imaging system, the MRI system, or the PET/CT imaging system can provide on-board imaging guidance 35.

In view of the above, a method of using the system 20 to irradiate a target in a patient under image guidance is also provided. The method comprises acquiring a 3-D image set of the patient in the treatment position before irradiation, developing a SIMAT plan or adjusting an existing SIMAT treatment plan based on the acquired images, and delivering the SIMAT treatment according to the plan by directing a focal dose of an intensity-modulated beam of radiation from an external source of radiation 24 at the target in the patient from numerous directions in a broad solid angle by (a) longitudinally rotating the external source of radiation 24, such as at least one external source of radiation, around a central axis and simultaneously or sequentially, in either order, latitudinally rotating the external source of radiation 24, such as at least one external source of radiation, or (b) longitudinally rotating the external source of radiation 24, such as at least one external source of radiation, around a central axis and simultaneously or sequentially, in either order, latitudinally rotating the external source of radiation 24, such as at least one external source of radiation, while continuously or discontinuously moving the patient. Optionally, x-ray projection images can be acquired during the treatment and used to adapt dynamically the treatment according to changes in the patient's anatomy.

A treatment plan can be, and preferably is, used to govern the movement of the globe gantry 21, the source of radiation 24, and the patient platform 28. The treatment plan is preferably designed by a treatment planning system that uses 3-D images of the patient and all the freedom provided by the system described herein to determine the best possible dose distribution. The planning procedure can, and typically does, involve computer optimization commonly referred to as "inverse planning." The treatment plan is then digitally transferred to the system 20 and translated to machine control code that drives the delivery of radiation and the movement of different components.

Figure 7:
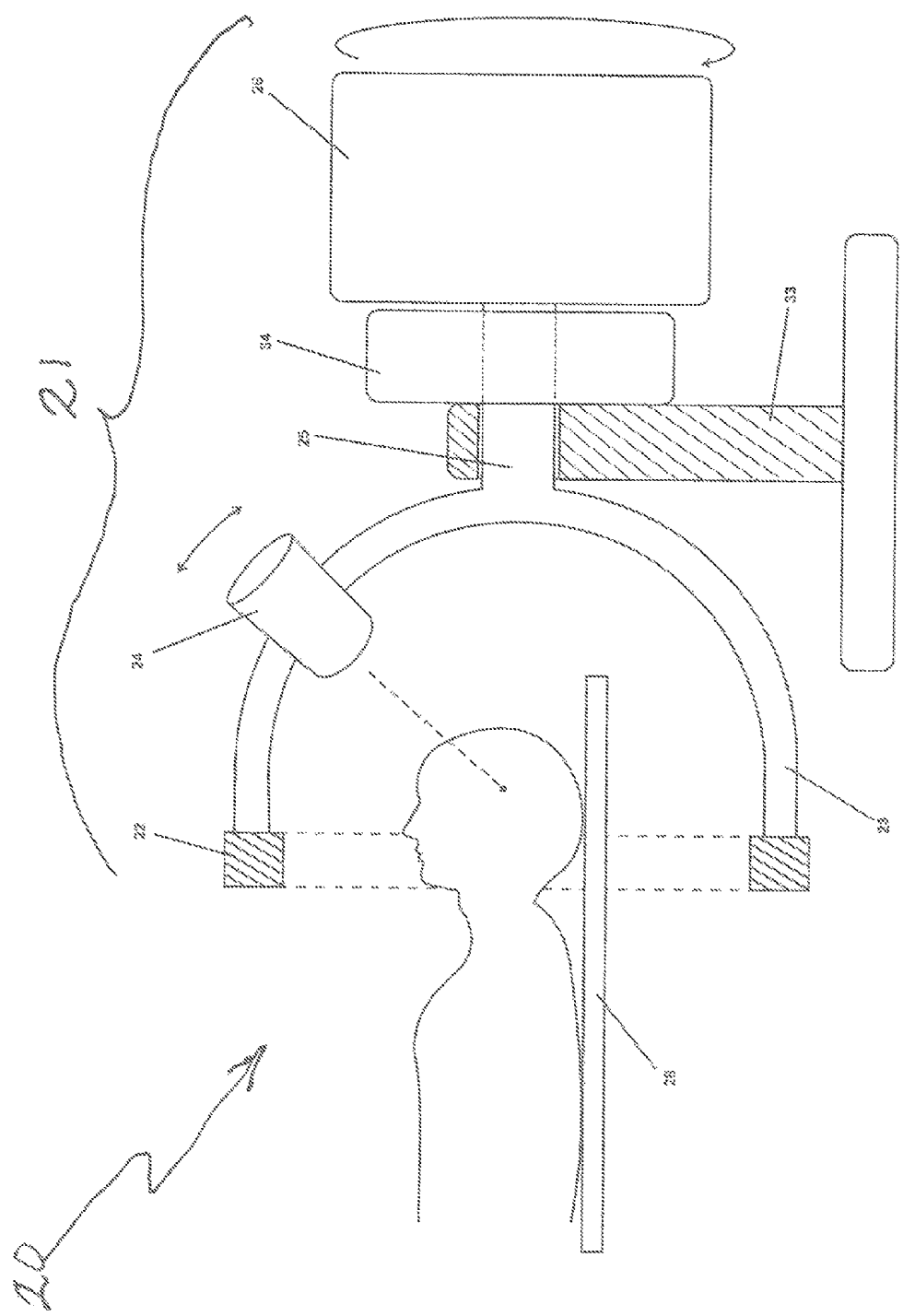
FIG. 7 partially illustrates a system 20 configured as a dedicated device for treating the brain and head and neck tumors where the ranges of the latitudinal angles at the front and rear ends of the globe gantry 21 are highly asymmetric about the transverse plane across the origin of the globe. Shown are the front opening ring 22, an arc-shaped, gantry support arm 23, an external source of radiation 24, a rear housing 26, a rear rotational axle 25 connected to a rotation-enabling device 34, such as a torque motor, and a patient platform 28. The entire globe gantry 21 is supported by a supporting column 33.

The system 20 and method can be configured to make stereotactic irradiation devices that are dedicated to a particular disease site. For example, by reducing the radius, R, of the front opening ring 22 of the globe gantry 21, the resulting system 20 can be used as an irradiation device dedicated for treating head (e.g., brain) and neck tumors as shown in FIG. 7, which illustrates a system 20 configured as a dedicated device for treating the brain and head and neck tumors where the ranges of the latitudinal angles at the front and rear ends of the globe gantry 21 are highly asymmetric about the transverse plane across the origin of the globe. In this clinical application, most or all beams would be directed from the rear hemisphere of the globe gantry. The smaller radius, R, allows the dose rate to be increased. The ranges of the latitudinal angles of the globe gantry 21 can be smaller than the general purpose systems, for example, from about 40° to about 110°, making most beams aiming from the superior side of the patient. Because the radius is smaller, the globe gantry 21 weighs less, and the supporting structures can be simplified by using, for example, a single, central supporting column 33. For example, a torque motor 34 with its stator fixed to the support column 33 and its rotor fixed to the rear, rotational axle can be used to drive the longitudinal rotation. One of ordinary skill in the art can use different mechanisms from the torque motor 34 to effect longitudinal rotation. The supporting base 27 below the front opening ring 22 can be eliminated. The rear, stationary housing 26, which contains the power supply and the controller for the radiation head, can rotate with the globe gantry 21, thereby eliminating the need for a slip ring for electrically connecting the stationary power supply and controller to the radiation head. The patient naturally looks out the front opening. The latitudinal range can take further advantage of the geometry of the human head such that most or all beams enter from the upper hemisphere of the head, coinciding with the rear end of the globe gantry 21.

Figure 8:
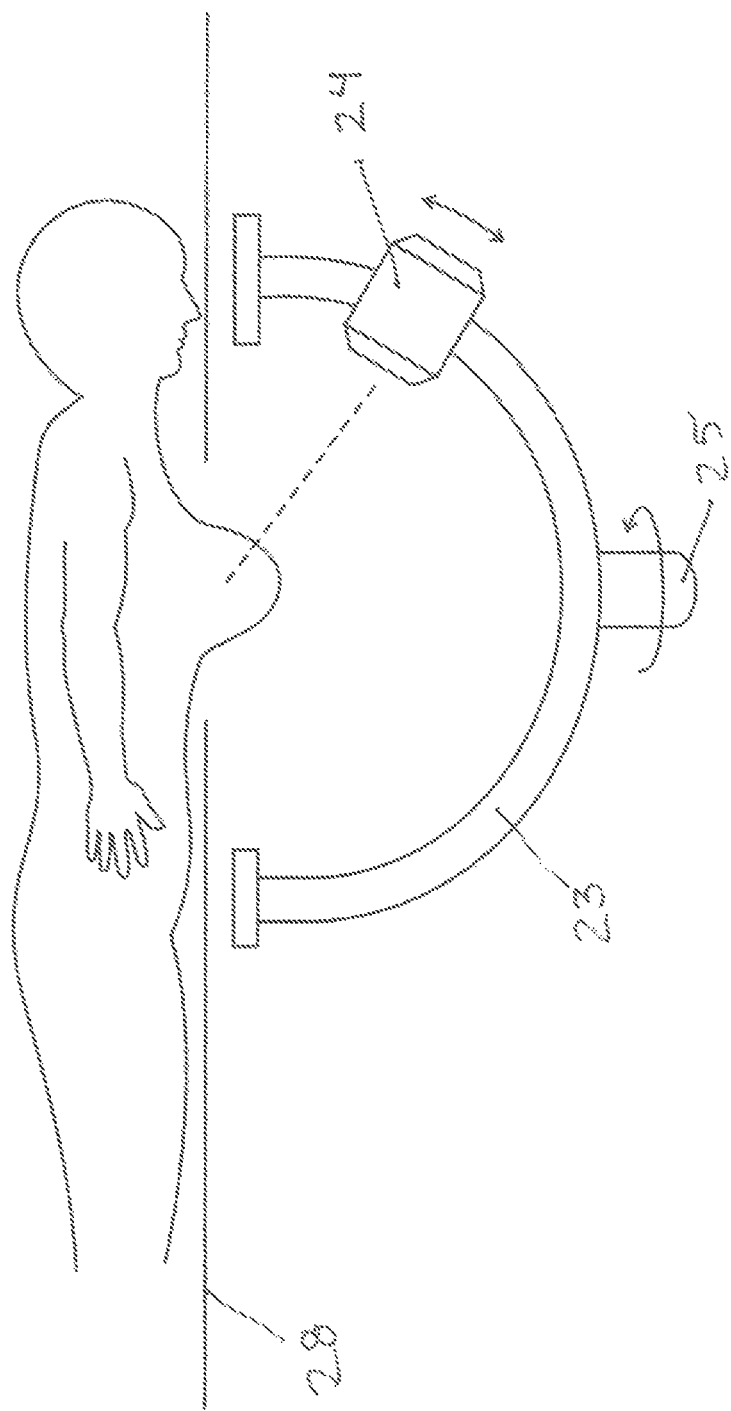
FIG. 8 partially illustrates a system 20 configured as a dedicated device for treating cancers in a human breast pendent through an opening in a patient platform 28 positioned above the opening of the globe gantry, the longitudinal axis of rotation of which is vertical. Shown are an arc-shaped, gantry support arm 23, an external source of radiation 24, and a rear rotational axle 25.

If the front opening ring 22 of the globe gantry 21 is re-oriented and the radius, R, is optionally further reduced, the system 20 can be used for treating cancers in a human breast pendent through an opening in the patient platform 28 as shown in FIG. 8, which illustrates a system configured as a dedicated device for treating cancers in a human breast pendent through an opening in a patient platform 28 positioned above the opening of the globe gantry 21, the longitudinal axis of rotation of which is substantially vertical or vertical. The patient platform 28 lies above the front opening ring 22 and is supported and driven to make movements in all three directions (i.e., x, y and z axes).

Figure 9:
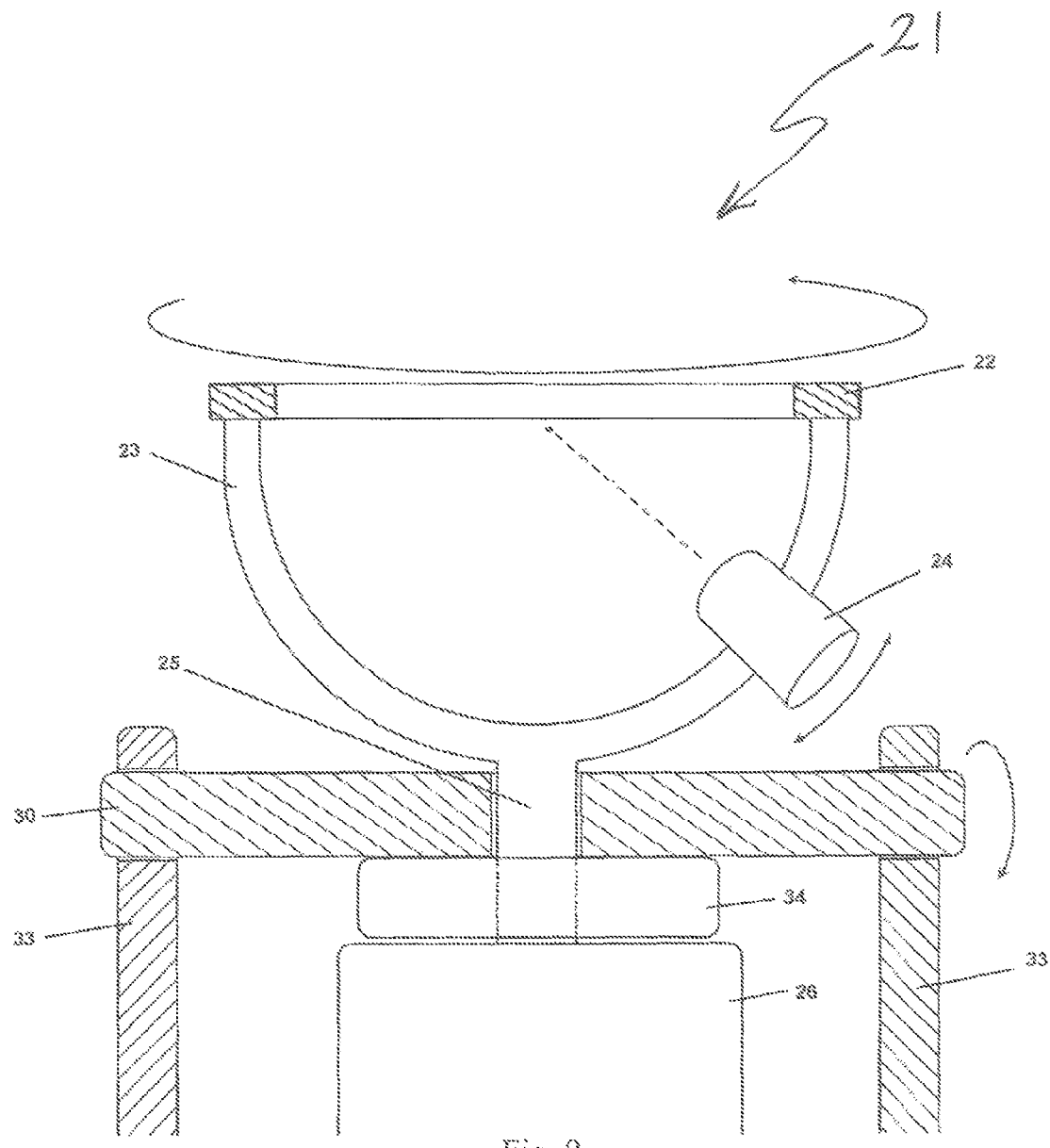
FIG. 9 illustrates an embodiment of the globe gantry 21 in which the longitudinal rotational axis can be pivoted between horizontal and vertical positions. A rear housing 26 comprises a source of power, mechanisms for moving components of the globe gantry, and controllers for controlling the movement of the components of the globe gantry and irradiation of the target in the patient. In this embodiment, the globe gantry 21 and rear housing 26 rotate together longitudinally by the torque motor 34 and pivot between horizontal and vertical positions through the rotation of the pivoting axle 30 supported by two supporting columns 33. Shown are a front opening ring 22, an arc-shaped, gantry support arm 23, an external source of radiation 24, a rear rotational axle 25, a rear housing 26, a torque motor 34, and two supporting columns 33.

The globe gantries 21 of FIGS. 7 and 8 need not be two separate units. FIG. 9 illustrates an embodiment of the globe gantry 21 in which the longitudinal rotational axis can be pivoted between horizontal and vertical positions through the rotation of a pivoting axle 30 supported by two supporting columns 33. A rear housing 26, which comprises a source of power, mechanisms for moving components of the globe gantry 21, and controllers for controlling the movement of the components of the globe gantry 21 and the irradiation of the target in the patient, rotates longitudinally along with the globe gantry 21 by the torque motor 34 and pivots between horizontal and vertical positions along with the globe gantry 21. The ability to pivot the axis of longitudinal rotation allows the head/neck region and the breast, for example, to be treated with a single machine. The structure that supports the longitudinal rotational axle and the rear housing 26, which contains the power supply and controllers, is attached to a rotatable axle, which is supported, for example, by two supporting columns 33, which are separated enough for the rear housing 26 to swing in between the supporting columns 33, thereby allowing the longitudinal axis of the globe gantry 21 to be either horizontal or vertical for treatment of the head/neck and breast, respectively, for example.

Figure 10:
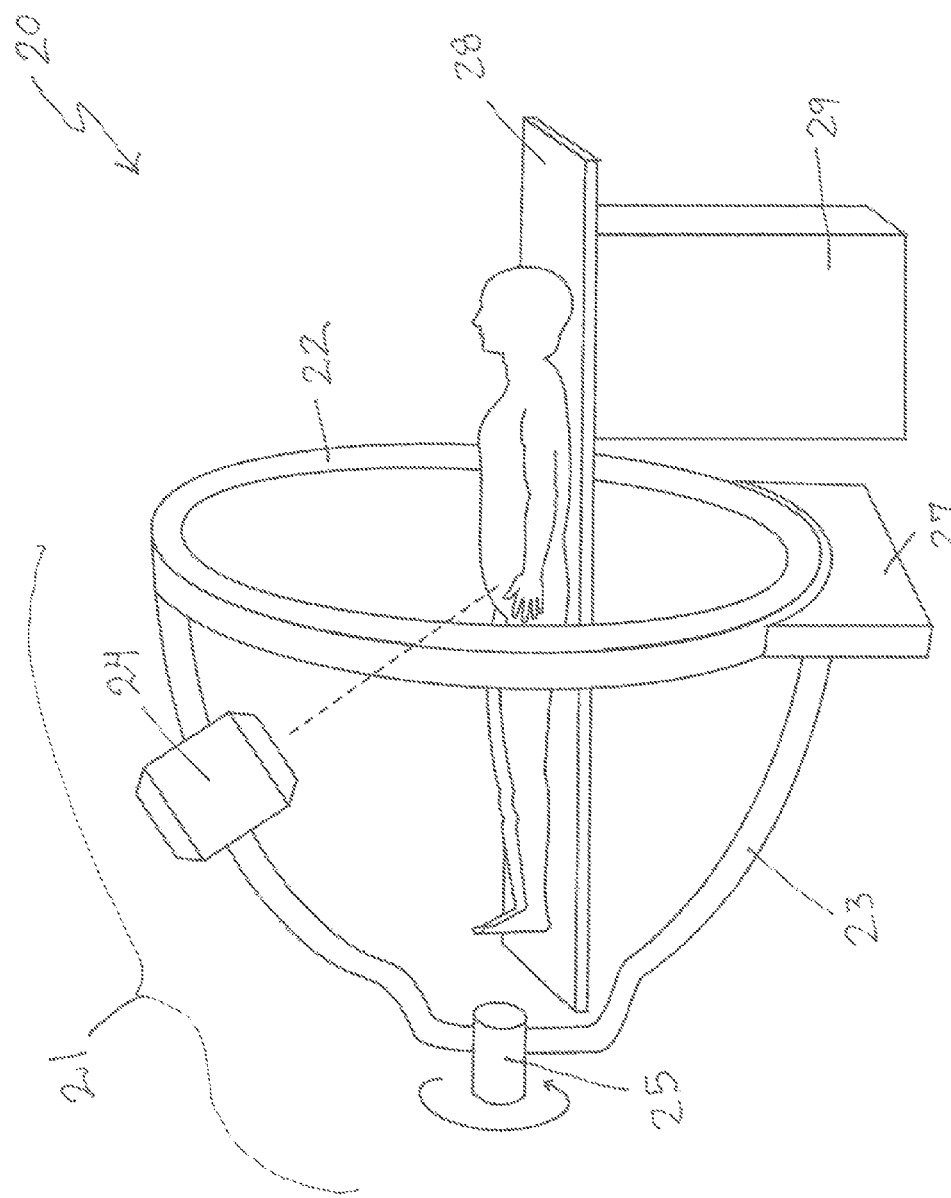
FIG. 10 illustrates an embodiment of the system 20 in which a recess at the rear end of the globe gantry 21 provides space for a patient's feet when treated in a "feet-in" orientation, such as for treatment of prostate cancer. The connection point for the rear axle 25 is at the rear end of the recess. Shown are a front opening ring 22, arc-shaped, gantry support arms 23, an external source of radiation 24, a support base 27, a patient platform 28, and a patient platform support 29.

The patient can be treated in either "head-in" or "feet-in" orientation. Therefore, the distance from the origin of the sphere (the isocenter) to the very rear end should not need to be substantially more than about 1 meter to allow irradiation of targets throughout the body. Since the use of beam directions substantially parallel to the patient's axis is not desired, the smallest latitudinal angle, φ, is about 40° (50° beyond the central transverse plane of the globe gantry). This allows additional space to be made available in the closed, rear end of the globe gantry 21 as shown in FIG. 10, which illustrates an embodiment of the globe gantry 21 in which a recess at the rear end of the globe gantry 21 provides space for a patient's feet when treated in a "feet-in" orientation, such as for treatment of prostate cancer. The connection point for the rear axle 25 is at the rear end of the recess. The beams used for treating pelvic/prostatic lesions can have an asymmetric latitudinal range, for example, of about 50° to about 110°, and can take advantage of the body's anatomy. Treatment of lesions in the torso section of a patient can have a symmetric latitudinal range, for example, of about 70° to about 110°.

By varying the starting and the stopping latitudinal angle of the source of radiation on the support beam(s), the boundary of the solid angle is defined. The latitudinal range for a given site also can vary with the longitudinal angle. For example, the latitudinal range anterior of the patient can be different from that posterior of the patient, thereby allowing customization to the patient's anatomy.

The terminology used herein is for the purpose of describing particular embodiments only and is not otherwise intended to be limiting.

All patents, patent application publications, journal articles, textbooks, and other publications mentioned in the specification are indicative of the level of skill of those in the art to which the invention pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising", "consisting essentially of", and "consisting of" may be replaced with either of the other two terms. Likewise, the singular forms "a", "an", and "the" include plural references unless the context clearly dictates otherwise. Thus, for example, references to "the method" include one or more methods and/or steps of the type described herein and/or apparent to those ordinarily skilled in the art upon reading the disclosure.

The terms and expressions, which have been employed, are used as terms of description and not of limitation. In this regard, where certain terms are defined and otherwise described or discussed elsewhere herein, all such definitions, descriptions, and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A globe gantry for longitudinally and latitudinally rotating at least one external source of radiation concentrically around an isocenter placed in a target to be irradiated in a patient, which globe gantry has a central axis intersecting the isocenter and which comprises:
- (i) a front opening ring with its origin on the central axis of the globe gantry,
- (ii) at least one arc-shaped, gantry support arm, which has a front end and a rear end and is part of a circle with its origin at the isocenter,
- (iii) an external source of radiation, which is mounted on at least one arc-shaped, gantry support arm of (ii), wherein the external source of radiation moves along the at least one arc-shaped, gantry support arm, thereby rotating latitudinally, and directing a beam of radiation at the isocenter,
- and optionally, a beam stopper, which is mounted on at least one arc-shaped, gantry support arm of (ii), and wherein the beam stopper is on an opposite side of the globe gantry from the external source of radiation,
- (iv) a rear rotational axle with an axis along the central axis of the globe gantry,
- (v) a support base, and
- (vi) a rear housing comprising a source of power, mechanisms for moving the globe gantry, and controllers for controlling movement of the globe gantry and the irradiation of the target in the patient, wherein the front opening ring is attached to the front end of the at least one arc-shaped, gantry support arm, wherein the rear rotational axle is attached to the rear end of the at least one arc-shaped, gantry support arm, wherein the front opening ring and the rear rotational axle are supported by the support base and the rear housing, and wherein the front opening ring and the rear rotational axle can rotate around the central axis.

2. The globe gantry of claim 1, wherein the external source of radiation is a linear accelerator or a radioisotope teletherapy device.

3. The globe gantry of claim 1, wherein the globe gantry can rotate about the central axis at a variable speed.

4. The globe gantry of claim 1, wherein the external source of radiation can move along the at least one arc-shaped, gantry support arm on which it is mounted at a variable speed.

5. The globe gantry of claim 1, wherein the orientation of the central axis of gantry rotation can be oriented horizontally, vertically, or substantially horizontally or vertically.

6. The globe gantry of claim 1, which comprises at least two arc-shaped, gantry support arms, which are separated by longitudinal angles of 180° or at least two pairs of adjacent arc-shaped, gantry support arms, which pairs are separated by longitudinal angles of 180°.

7. A system for irradiating a target in a patient, wherein said system comprises:
- (i) the globe gantry of claim 1,
- (ii) a patient platform, which comprises a first end and a second end and which is positioned along the central axis of the globe gantry or perpendicularly to the central axis of the globe gantry,
- (iii) a patient platform support, which supports the patient platform, and optionally,
- (iv) a patient shield.

8. The system of claim 7, wherein the patient platform can be independently moved in either direction along an axis parallel to a length of the patient platform or a z-dimension, in either direction along an axis parallel to a width of the patient platform or an x-dimension, and/or in either direction along an axis perpendicular to the patient platform or a y-direction and, as governed by a treatment plan, in coordination with movements of the globe gantry and the external source of radiation.

9. The system of claim 7, which further comprises:
- (v) at least two straight support beams,
- (vi) an x-ray tube, and
- (vii) an x-ray detector array, wherein the x-ray tube is mounted on at least one straight support beam of (v) on one side of the globe gantry, wherein the x-ray detector array is mounted on at least one straight support beam of (v) on the opposite side of the globe gantry from the x-ray tube, wherein the at least two straight support beams are parallel with the central axis of the globe gantry, and wherein the x-ray tube and the x-ray detector array are mounted at a longitudinal angle offset from the external source of radiation and, when present, the beam stopper, and wherein the x-ray tube and the x-ray detector array can move along the straight support beams to which the x-ray tube and the x-ray detector array are mounted.

10. The system of claim 9, wherein the x-ray detector array is one-dimensional or multi-dimensional.

11. The system of claim 7, which further comprises (v) a computed tomography (CT) imaging system, a magnetic resonance imaging (MRI) system, or a positron emission tomography (PET)/computed tomography (CT) imaging system positioned adjacent to the front opening ring of the globe gantry, wherein the CT imaging system, the MRI system, or the PET/CT imaging system can provide on-board volumetric imaging guidance.

12. A method of irradiating a target in a patient using the system of claim 7, wherein said method comprises:
creating a focal radiation dose by directing intensity-modulated beams of radiation from the external source of radiation at the target in the patient in a treatment position from numerous directions in a broad solid angle by (a) longitudinally rotating the external source of radiation around the central axis and simultaneously or sequentially, in either order, latitudinally rotating the external source of radiation back and forth, or (b) latitudinally rotating the external source of radiation around the central axis and simultaneously or sequentially, in either order, longitudinally rotating the external source of radiation back and forth, while continuously or discontinuously moving the patient, whereupon the target in the patient is irradiated.

13. The method of claim 12, wherein the system further comprises (v) either (a) at least one straight support beam, an x-ray tube, and an x-ray detector array, wherein the x-ray tube is mounted on at least one of the at least one straight support beam on one side of the globe gantry, wherein the x-ray detector array is mounted on at least one of the at least one straight support beam on the opposite side of the globe gantry from the x-ray tube, wherein the straight support beams are parallel with the central axis of the globe gantry, and wherein the x-ray tube and the x-ray detector array are mounted at a longitudinal angle offset from the external source of radiation and, when present, the beam stopper, and wherein the x-ray tube and the x-ray detector array can move along the straight support beams to which the x-ray tube and the x-ray detector array are mounted, or (b) a CT imaging system, an MRI system, or a PET/CT imaging system positioned adjacent to the front opening ring of the globe gantry, and, when (b), the method further comprises acquiring before irradiation a 3-D image set of the patient positioned on the patient platform in the treatment position, developing a treatment plan or adjusting an existing treatment plan based on the acquired image set, and directing a focal dose of an intensity-modulated beam of radiation from the external source of radiation at the target in the patient in accordance with the treatment plan.

* * * * *